United States Patent
Crisp

(10) Patent No.: US 11,305,054 B2
(45) Date of Patent: Apr. 19, 2022

(54) PRESSURIZED WATER FLUID DISTRIBUTION

(71) Applicant: Jackson L. Crisp, Moorcroft, WY (US)

(72) Inventor: Jackson L. Crisp, Moorcroft, WY (US)

(\*) Notice: Subject to any disclaimer, the term of this patent is extended or adjusted under 35 U.S.C. 154(b) by 383 days.

(21) Appl. No.: 16/150,092

(22) Filed: Oct. 2, 2018

(65) Prior Publication Data
US 2019/0143028 A1  May 16, 2019

Related U.S. Application Data

(60) Provisional application No. 62/585,404, filed on Nov. 13, 2017.

(51) Int. Cl.
| | | |
|---|---|---|
| *A61M 31/00* | (2006.01) | |
| *A61M 3/02* | (2006.01) | |
| *F16K 21/00* | (2006.01) | |
| *F16K 11/00* | (2006.01) | |

(52) U.S. Cl.
CPC .......... *A61M 3/0258* (2013.01); *A61M 3/022* (2014.02); *A61M 3/025* (2013.01); *A61M 3/0208* (2014.02); *A61M 3/0279* (2013.01); *F16K 11/00* (2013.01); *F16K 21/00* (2013.01)

(58) Field of Classification Search
CPC .. A61M 3/0279; A61M 3/0208; A61M 3/022; A61M 3/025; A61M 3/02
See application file for complete search history.

(56) References Cited

U.S. PATENT DOCUMENTS

| | | | | |
|---|---|---|---|---|
| 3,004,537 A | * | 10/1961 | Turliuc | A61M 9/00 604/248 |
| 3,162,193 A | * | 12/1964 | Zacks | A61M 3/0241 604/262 |
| 4,178,931 A | | 12/1979 | Lind et al. | |

(Continued)

FOREIGN PATENT DOCUMENTS

| | | | |
|---|---|---|---|
| BR | PI1102182 A2 * | 6/2013 | .............. F16L 17/10 |
| CN | 202515816 U | 11/2012 | |
| WO | 2012159177 A1 | 11/2012 | |

OTHER PUBLICATIONS

Claber, "8583 Koala Indoor Faucet Adapter US" Dec. 22, 2016, Retrieved online from https://www.youtube.com/watch?v+m_-mxQD9hBA on Nov. 30, 2018, 1 Page.

(Continued)

*Primary Examiner* — Rebecca E Eisenberg
(74) *Attorney, Agent, or Firm* — Goff IP Law PLLC; Jared Goff

(57) ABSTRACT

A fluid distribution system can include a water inlet configured to receive water from a supply spout. A supply line can be connected to the inlet, and an applicator tip can be connected to the supply line distal from the inlet. The applicator tip can be configured to spray water received through the supply line at the same time as the receiving of the water from the supply spout through the inlet. The system can further include a water pressurizing device that is operable to pressurize water received from the supply spout via the water inlet and supplied through the supply line to the applicator tip. The water pressurizing device can include one or more of a powered fluid pump and a source adapter. The system may include a fluid-actuated pressure clamp.

9 Claims, 15 Drawing Sheets

(56) References Cited

U.S. PATENT DOCUMENTS

| | | | |
|---|---|---|---|
| 4,284,078 A | 8/1981 | Pace | |
| 4,622,704 A | 11/1986 | Chung | |
| 4,941,459 A | 7/1990 | Mathur | |
| 5,199,945 A | 4/1993 | Chu | |
| 7,666,171 B2 | 2/2010 | Mombrinie et al. | |
| 8,425,475 B2 | 4/2013 | Sodo | |
| 2007/0257137 A1* | 11/2007 | Darling, III | B05B 9/0816 239/587.1 |
| 2009/0121042 A1 | 5/2009 | Mitry | |
| 2011/0302709 A1 | 12/2011 | Taylor et al. | |

OTHER PUBLICATIONS

International Search Report, International Patent Application No. PCT/US 18/54011, International Filing Date Oct. 2, 2018, dated Dec. 20, 2018, 10 Pages.

\* cited by examiner

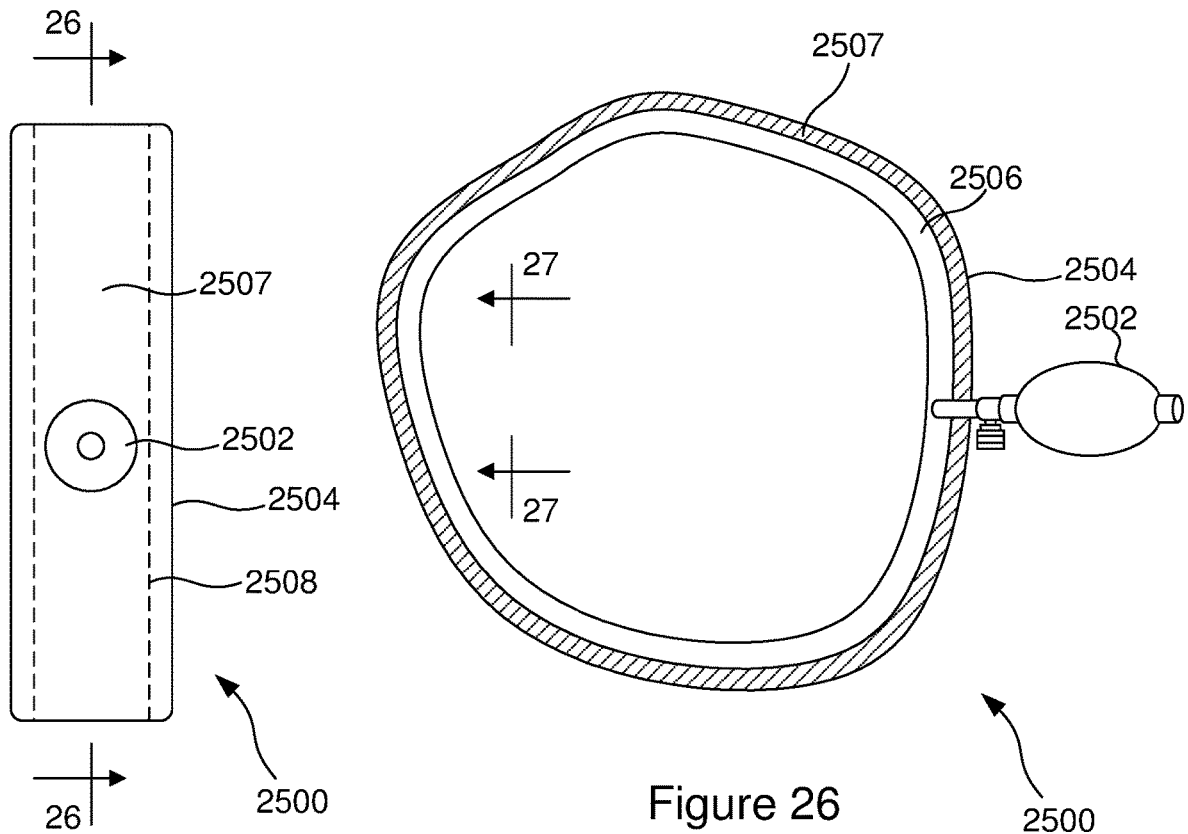
Figure 25
Figure 26
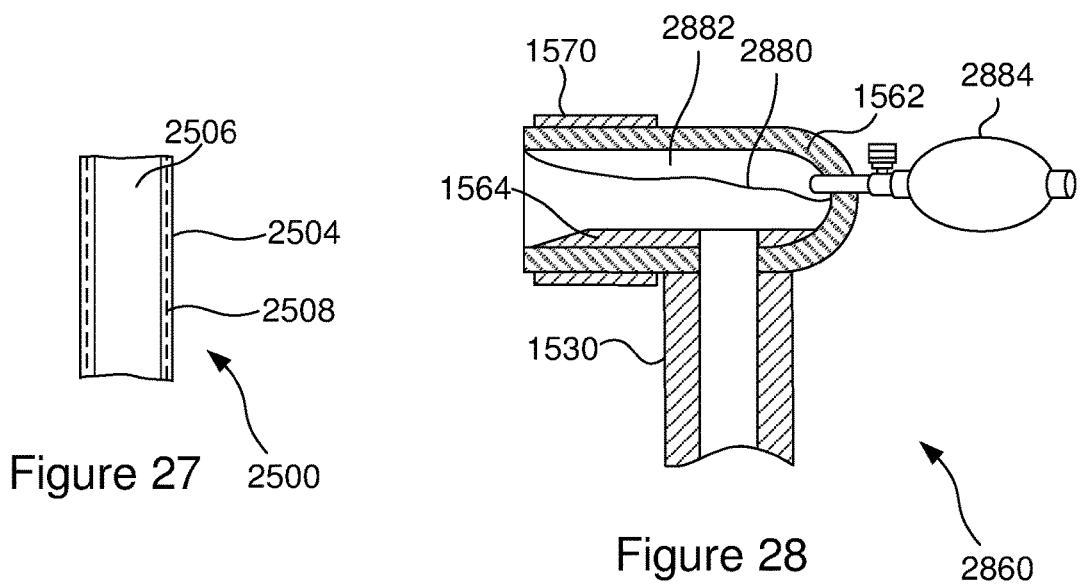
Figure 27
Figure 28

PRESSURIZED WATER FLUID DISTRIBUTION

RELATED APPLICATIONS

The present application claims the benefit of U.S. provisional patent application No. 62/585,404, filed Nov. 13, 2017, and entitled "Portable Universal Pressurized Water-Fluid Distribution System", which is incorporated herein by reference. If any disclosures are incorporated herein by reference and such incorporated disclosures conflict in part or whole with the present disclosure, then to the extent of conflict, and/or broader disclosure, and/or broader definition of terms, the present disclosure controls. If such incorporated disclosures conflict in part or whole with one another, then to the extent of conflict, the later-dated disclosure controls.

BACKGROUND

Currently, when a user wants to perform a self-enema there are typically three options. The first is to install, typically in the shower, a more permanent enema system, typically involving tools, threaded piping materials, heavier-duty hose, fittings and flow splitters (allowing water to be diverted to the enema system and/or to the shower-head), regulators (used to set the volume of flow) and multi-use (typically interchangeable) application tips. The second is typically intended to be a more portable and limited use option, composed of capacity and pressure limited water bags and/or reservoirs (enema water source) connected to similar but significantly less robust (low pressure rated) tubing (hose), connectors, fittings and (typically uncomfortable low pressure) applicator tips, as compared to the first option. The third option, similar to the second, is portable and includes an applicator tip connected to a removable, refillable, and significantly capacity limited, squeeze bulb water reservoir.

SUMMARY

The present application discusses fluid distribution system features that can include improved connections between fluid conduits, and an improved fluid distribution system that can be used to distribute pressurized water. For example, the fluid can be water from water spouts, and a system may distribute water from a faucet or shower head to an applicator for personal hygienic flushing. The application also discusses novel clamping systems that may be used with the overall fluid distribution systems discussed herein, or they may be used in other systems and devices. Regardless, the fluid distribution systems and the clamping systems discussed herein provide new features and benefits not present in prior systems. They systems herein can be used for liquid fluids, such as water, which may include other materials with the water, such as where other medicinal fluids are infused in the water.

According to one embodiment, a technique for using a water fluid distribution system can include receiving water from a supply spout through an inlet, with the supply spout being one of a water faucet spout or a shower head. The water can be passed through a supply line connected to a personal hygienic flushing applicator tip. The water can also be passed from the supply line and through the applicator tip, with the water that is passed through the applicator tip exiting the water fluid distribution system at the same time as the receiving of the water from the supply spout through the inlet (i.e., some portion of the water can be received from the supply spout through the inlet at the same time as another portion of the water is exiting the water fluid distribution system through the applicator tip). The water can be pressurized using a water pressurizing device, with the passing of the water from the supply spout through the applicator tip including passing the pressurized water through the applicator tip, and with the water pressurizing device including one or more of a powered fluid pump and a source adapter that is fluidly sealed to the supply spout, with the source adapter being conformable to match multiple different shapes of corresponding supply spouts.

According to another embodiment, a technique can include positioning a first conduit adjacent to a second conduit. The technique can further include fluidly sealing the first conduit to the second conduit. The fluidly sealing can include positioning a fluid clamp in a sealing position. The fluidly sealing can further include, with the fluid clamp in the sealing position, forcing pressurized fluid, such as air, from a pressurized fluid source into a bladder of the fluid clamp. The pressurized fluid can inflate the bladder, with the bladder pressing a pair of sealing surfaces against each other when the bladder is inflated.

According to yet another embodiment, a water fluid distribution system can include a water inlet configured to receive water from a supply spout that is one of an in-sink water faucet spout or a shower head. A supply line can be connected to the inlet, and an applicator tip can be connected to the supply line distal from the inlet. The applicator tip can be configured to spray water received through the supply line at the same time as the receiving of the water from the supply spout through the inlet. The system can further include a water pressurizing device that is operable to pressurize water received from the supply spout via the water inlet and supplied through the supply line to the applicator tip. The water pressurizing device can include one or more of a powered fluid pump and a source adapter, with the source adapter having a conformable adapter sealing surface that is conformable to multiple different shapes of corresponding supply spout sealing surfaces.

According to yet another embodiment, a fluid pressure clamp system can include a fluid clamp. The fluid clamp can include a bladder and a pressurized fluid source connected to the bladder. The clamp can be configured to fluidly seal a first conduit to a second conduit, with the fluid clamp being configured to receive pressurized fluid from the pressurized fluid source to inflate the bladder of the fluid clamp, and with the bladder being configured to press a pair of sealing surfaces against each other when inflated to fluidly seal the first conduit to the second conduit.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

FIG. 25 is a view of a fluid-actuated clamp.

FIG. 26 is a partially sectioned view taken along line 26-26 of FIG. 25.

FIG. 27 is a broken away view taken along line 27-27 of FIG. 26.

FIG. 28 is a partially sectioned view of yet another supply spout adapter fluid distribution system that is not currently connected to a supply spout.

The description and drawings may refer to the same or similar features in different drawings with the same reference numbers.

DETAILED DESCRIPTION

The features discussed herein provide improvements in fluid distribution systems, including providing advantageous features for clamping conduits together, and advantageous features in delivery systems for distributing water from faucets and shower heads to personal hygienic flushing applicators.

The features of a personal hygienic flushing distribution system can include systems that allow for pressurizing and delivering water from various different shapes of faucets or shower heads to personal hygienic flushing applicators. This can be done in a manner that allows the water to be provided from the faucet or shower head while water is delivered through the flushing applicator. The distribution system can be arranged to be portable and to be easily installed for use with different shapes of faucets and/or shower heads. In embodiments discussed herein, the pressurizing of the water to be delivered can be done using a fluid pump, and/or an adapter. The adapter can conform to the shape of the faucet or shower head so that pressure of water in the faucet or shower head can be maintained.

I. RESERVOIR-PUMP FLUID DISTRIBUTION SYSTEM EXAMPLES

Figure 1:
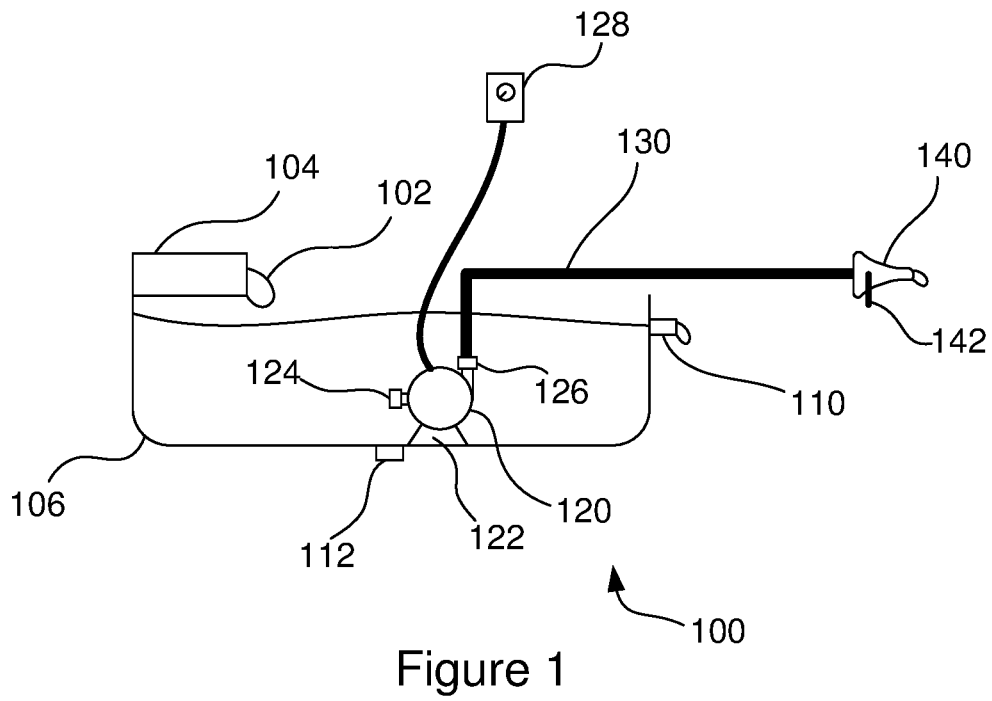
FIG. 1 is a partially sectioned side view of a reservoir-pump water distribution system.

Referring to FIG. 1, a partially sectioned side view of a reservoir-pump water distribution system (100) is illustrated for distributing water (102) from a supply spout (104). The system (100) can receive water from the supply spout (104). As an example, the supply spout (104) can be a standard bathroom sink faucet. As discussed here, the supply spout (104) and a reservoir (106) will be discussed as being part of the distribution system (100). However, the supply spout (104) and/or the reservoir (106) may or may not be considered part of the fluid distribution systems to be included in the claims discussed below, depending on the language of the claims themselves. The supply spout (104) can be configured to provide water (102) to a reservoir (106). In the illustrated example, the reservoir (106) can be a bathroom sink basin. The reservoir (106) can include an overflow drain (110) which can be, for example, a standard overflow drain in a bathroom sink basin. The reservoir (106) can also include a main drain (112), such as a bottom drain in a bathroom sink basin.

The system (100) can include a portable fluid pump (120), which can be submerged in the water (102) in the reservoir (106). The pump (120) can be a submersible pump. Also, as with other pumps discussed herein, the pump (120) may include one or more pump mounts (122) to releasably secure the pump (120) to a solid surface, such as to the reservoir (106) in the embodiment of FIG. 1. For example, the pump may include one or more suction cups attached to the pump (120), to secure the pump (120) to the reservoir (106) during use. As with the other pumps discussed herein, the pump (120) may be any of various different types of pumps, so long as the pump can receive water through an inlet (124) and can emit water at a safe and sufficient pressure and flow rate through an outlet (126). The pump (120) may be an electric pump, such as a pump that can be powered by a standard household electrical outlet and/or by batteries. The system (100) may further include a variable power regulator (128) for the pump (120). For example, the power regulator (128) may be an AC to DC power converter, or adapter, that plugs into a standard alternating current electrical outlet and provides direct current power to the pump (120). The power regulator (128) can include a handle, such as a rotatable knob or a slider that can be actuated to adjust the amount of electrical power provided to the pump (120) (such as by adjusting the direct current voltage provided to the pump (120)). Also, the pump (120) may be positioned in a dip (not shown) in the bottom of the reservoir (106), which can lower the inlet (124) of the pump (120).

The system (100) can further include a supply line (130), which can include one end that is fluidly sealed and attached to the outlet (126) of the pump (120) and another end that is fluidly sealed and attached to a personal hygienic flushing applicator tip (140). The system may include a variable flow regulator (142) that is located upstream of the applicator tip (140) or is built into the applicator tip (140). The flow regulator (142) may be a valve that can be opened to varying degrees using an attached handle. The flow of water (102) through the applicator tip (140) may be adjusted using the power regulator (128) and/or the flow regulator (142) to assure sufficient flow through the system while still maintaining an adequate level of water (102) in the reservoir (106). In some embodiments, one or more of the power regulator (128) and the flow regulator (142) may be omitted. Also, the power regulator (128) (in embodiments that include a pump) and/or the flow regulator (142) (in any of the embodiments) may be included in the embodiments discussed below. As with other supply lines discussed herein, the supply line (130) can be a standard fluid supply line. For example, the supply line (130) can be a flexible supply line, such as a hose formed of an elastomer or rubber material, though at least part of the supply line (130) may be rigid. Also, as with other supply lines discussed herein, the supply line (130) can be connected and sealed to other components (the outlet (126) of the pump (120) and the applicator tip (140) in this embodiment) using standard fluid connectors, such as threaded and/or non-threaded connectors and/or clamping devices such as standard hose clamps.

Referring still to FIG. 1, assembly and use of the system (100) will be discussed. In assembling the system (100), supply line (130) can be connected to the pump (120) and to the applicator tip (140), so that the supply line is fluidly sealed at each of its ends. The reservoir (106) and any other components that may be unsanitary can be sanitized prior to use, such as by using standard cleaning techniques, such as wiping the reservoir (106) with sanitizing wipes or using a wipe cloth or sponge with spray-on sanitizing cleaner. The pump (120) can be mounted in the reservoir (106), and the supply spout can be turned on to supply water (102) to the reservoir (106). The water (102) can continue to flow into the reservoir (106) until the water (102) spills over the overflow drain (110) of the reservoir (106). Thus, water level in the reservoir (106) can reach a steady state with water flowing into the reservoir (106) from the supply spout (104), and out of the overflow drain (110). With this steady state established, the pump (120) can be turned on, thereby providing a constant stream of pressurized water (102) to the applicator tip (140) for use, such as in personal hygienic flushing activities. For example, such flushing activities may include conducting enemas, douching, or conducting dental water pick activities.

For different types of such activities, different types of applicator tips (140) (e.g., douche applicator tips, enema applicator tips, and/or dental pick applicator tips) may be used. Moreover, such different types of applicator tips (140) may be used interchangeably with the same system (100), by replacing one applicator tip with another. Such applicator tip replacement can also include cleansing of the applicator tip (140) and/or other portions of the system (100) to maintain sanitation of the system (100).

During use, the pump (120) can continue drawing water (102) from the reservoir (106) and supplying the water (102) in pressurized form to the applicator tip (140). The flow rate of water (102) from the supply spout (104) can be set to meet or exceed the flow rate of water (102) from the pump (120), so that the reservoir (106) remains full during use. The supply spout (104) can supply water (102) to the reservoir (106) while the pump (120) supplies water (102) to the applicator tip (140). However, the supply spout (104) may be turned off during a portion of the time the pump is supplying water (102) to the applicator tip (140) in some scenarios. In some embodiments, it can be preferable to keep the level of water (102) in the reservoir (106) above the level of the inlet (124) of the pump (120).

When the use activity is completed, the pump (120) can be turned off, and the supply spout (104) can also be turned off. The water (102) can be drained from the reservoir (106) and from other components of the system (100), such as the pump (120), the supply line (130), and the applicator tip (140). The components of the system (100) can also be cleaned. The portable components of the system (100) can be put away in a container. For example, the pump (120), the supply line (130), and the applicator tip (140) can all be placed in a portable container.

Figure 2:
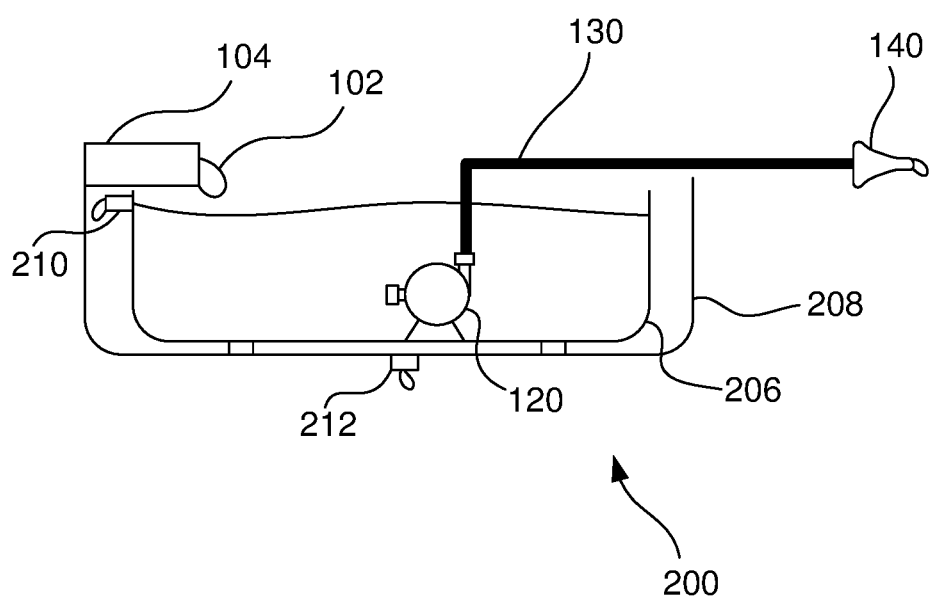
FIG. 2 is a partially sectioned side view of another reservoir-pump water distribution system.

Referring to FIG. 2, another embodiment of a reservoir-pump water distribution system (200) will be discussed. The system (200) can be similar to the system (100) of FIG. 1, including having a supply spout (104), a pump (120), a supply line (130), and an applicator tip (140). However, the system (200) can include a reservoir (206) that is seated in an overflow container (208). For example, the overflow container (208) can be a standard bathroom sink basin. The inner reservoir (206) can be a container that is sized to be seated at least partially within the overflow container (208). As an example, the inner reservoir (206) may be a rigid container made of a polymer, metal, ceramic or similar type of material. Alternatively, the inner reservoir (206) may be a more flexible container, such as a flexible liner that conforms to at least a portion of a contour of the overflow container (208). The inner reservoir (206) can have an overflow drain (210) that can empty overflowing water (102) into the overflow container (208). The overflow container (208) can include a main drain (212) through which water that empties into the overflow container (208) can drain.

The inner reservoir (206) can be positioned to receive water (102) from the supply spout (104) and to receive the pump (120) at least partially within the reservoir (206) during use. Assembly, disassembly, and use of the system (100) can be similar to the system (100) above. However, the inner reservoir (206) can be placed in the outer overflow container (208) prior to use. Also, water (102) can be emptied from the inner reservoir (206) after use (e.g., poured into the overflow container (208)). The inner reservoir (206) can be portable, and may be stored and/or transported in a container along with the pump (120), supply line (130), and applicator tip (140). Notably, even if the reservoir (206) is transported, it may be smaller than reservoirs in some prior systems, because the water in the reservoir (206) can be replenished with water from the supply spout (104) while the system (200) is supplying pressurized water to the applicator tip (140).

Different embodiments of reservoir-pump water distribution systems will be discussed with reference to FIGS. 3-6. In each of these, a reservoir is illustrated but no supply spout is illustrated. These distribution systems can have water supplied from a supply spout to the reservoir, as in the embodiments of FIGS. 1-2. Also, each of the reservoirs may be configured as a reservoir without an additional overflow container in the system, as in the illustration of FIG. 1, or as an inner reservoir with an additional overflow container, as in FIG. 2. Each of these systems of FIGS. 3-6 can also include a pump (120), a supply line (130), and an applicator tip (140) like those discussed above with reference to FIGS. 1-2.

Figure 3:
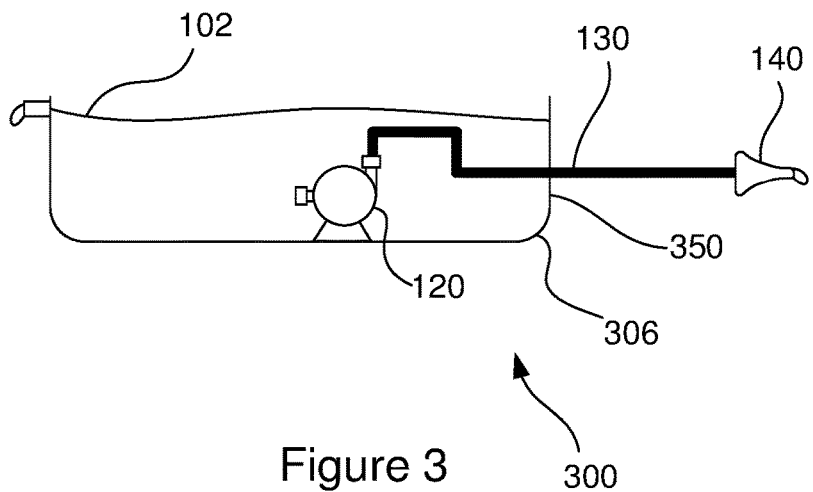
FIG. 3 is a partially sectioned side view of yet another reservoir-pump water distribution system.

Referring now to FIG. 3, a reservoir-pump water distribution system (300) can include a reservoir (306), with the pump (120) positioned in the reservoir (306) during use. The supply line (130) can extend through a wall (350) of the reservoir (306) and continue to the applicator tip (140). A connector (not shown) may be secured to the wall (350) of the container. The supply line (130) in this embodiment may include one section that extends from the pump (120) to the connector on the wall (350) and another section that extends from the connector on the wall (350) to the applicator tip (140). For example, the connector on the wall (350) may be a threaded connector that mates with threaded connectors on the sections of the supply line (130). In this embodiment of FIG. 3, assembly and disassembly of the system (300) may include connecting and disconnecting the sections of the supply line (130) from the reservoir (306).

Figure 4:
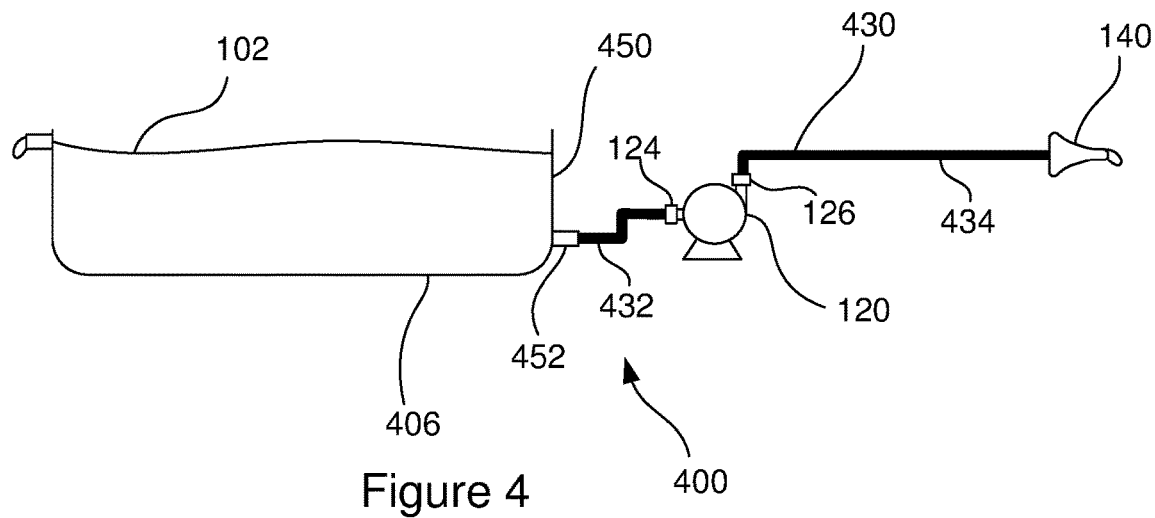
FIG. 4 is a partially sectioned side view of yet another reservoir-pump water distribution system.

Referring now to FIG. 4, reservoir-pump water distribution system (200) can include a reservoir (406) that includes a wall (450) with an outlet port (452) secured to the wall so that water (102) can pass from inside the reservoir (406), through the outlet port (452), and into a supply line (430). The supply line (430) can include a pre-pump supply line (432) that extends from the outlet port (452) to an inlet (124) of the pump (120), with the pre-pump supply line (430) being fluidly sealed to the outlet port (452) and to the inlet (124) of the pump (120). The supply line (430) can also include a post-pump supply line (434) that extends from the outlet (126) of the pump (120) to the applicator tip (140), with the post-pump supply line (434) being fluidly sealed to the pump outlet (126) and to the applicator tip (140). The pump (120) of the system (400) need not be pump that is designed to be submerged, but it can be in some examples. The system (400) can be assembled, disassembled, and used similarly to the systems discussed above. However, the assembly and disassembly can include connecting and disconnecting the sections of the supply line (430) from the reservoir (406), the pump (120), and the applicator tip (140).

Figure 5:
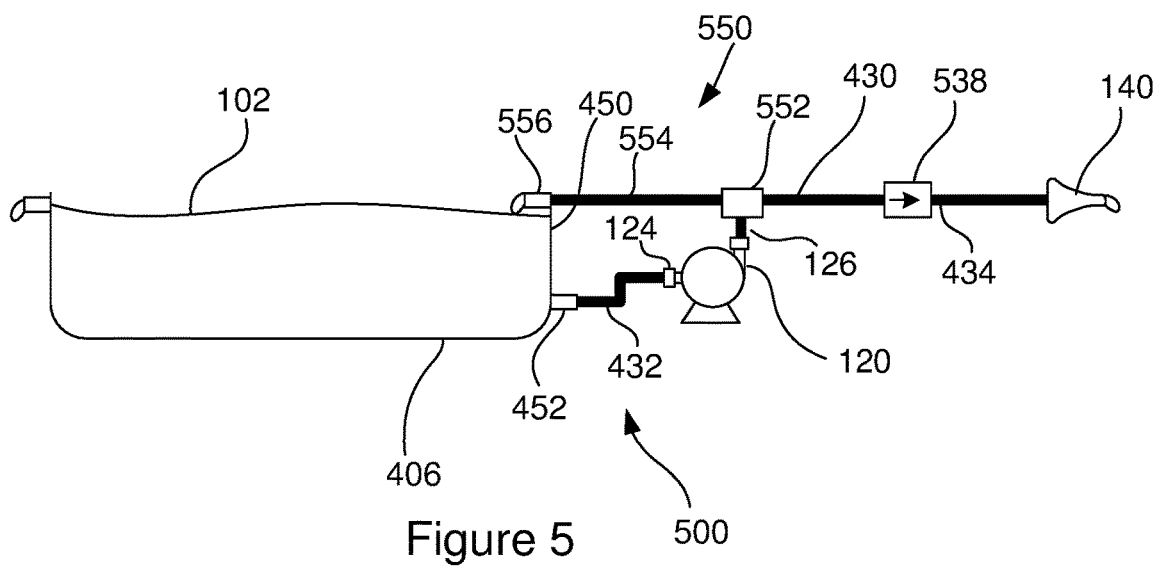
FIG. 5 is a partially sectioned side view of yet another reservoir-pump water distribution system.

Referring now to FIG. 5, another example of a reservoir-pump water distribution system (500) will be discussed. The system (500) of FIG. 5 can be similar to the system (400) of FIG. 4, but with the addition of a pump recirculation system (550). The pump recirculation system (550) can recirculate water (102) back into the reservoir (406) when flow is restricted or cut off somewhere between the pump outlet (126) and the outlet of the applicator tip (140). For example, this can be advantageous for use with pumps that are not optimally designed to function with flow idle or deadheading in response to flow being restricted or cut off. In the illustrated embodiment, the system (500) can include a one-way valve (538) in the post-pump supply line (434) to prevent water from backflowing through the pump recirculation system (550) from the applicator tip (140). Such a one-way valve can be included in other embodiments as well, to similarly prevent backflow from the applicator tip (140). The pump recirculation system (550) can include a pressure relief valve (552) positioned in the post-pump supply line (434) upstream from the one-way valve (538). A recirculation line (554) can extend from the pressure relief valve (552) to a recirculation port (556) in the reservoir (406). Thus, if pressure in the post-pump supply line (434) exceeds a threshold pressure of the pressure relief valve (552), the pressure relief valve (552) can open to allow water (102) to flow through the recirculation line (554), through the recirculation port (556) and back into the reservoir (406). The recirculation system (550) can thereby relieve pressure downstream of the pump (120). Such a recirculation system (550) can be used in other different embodiments as well.

Figure 6:
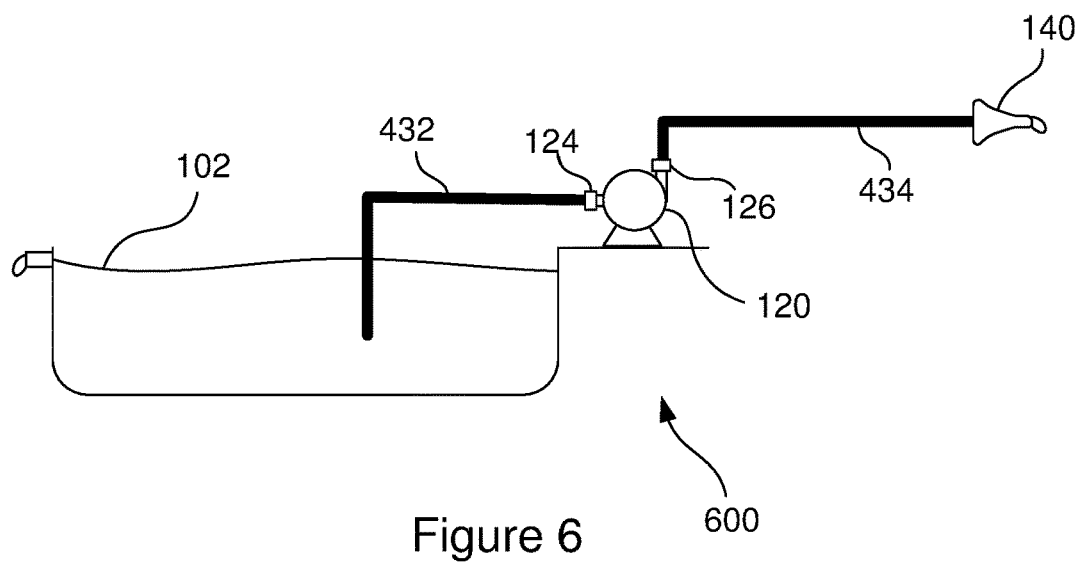
FIG. 6 is a partially sectioned side view of yet another reservoir-pump water distribution system.

Referring now to FIG. 6, another example of a reservoir-pump water distribution system (600) is illustrated. The system (600) can be similar to the system (400) discussed above, except that the pre-pump supply line (432) can go down into the water (102) in the reservoir (406) through an open water surface, rather than receiving water (102) through the outlet port (452) of the reservoir (406).

Figure 7:
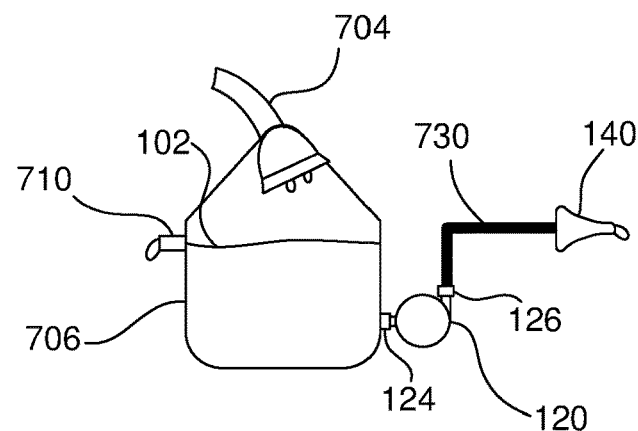
FIG. 7 is a partially sectioned side view of yet another reservoir-pump water distribution system.
Figure 7:
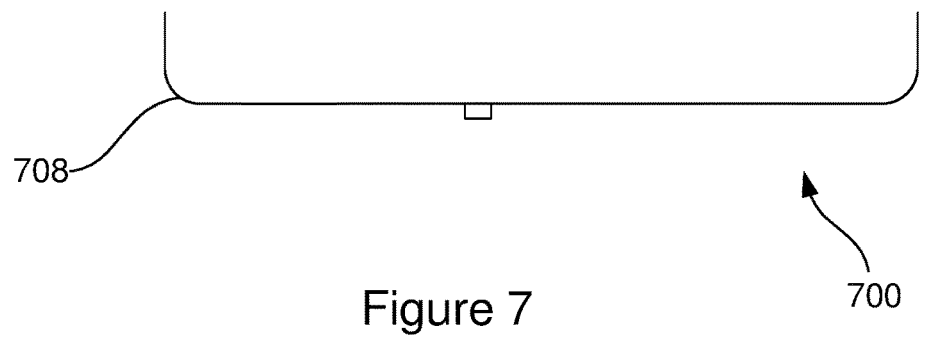

Referring now to FIG. 7, another embodiment of a reservoir-pump water distribution system (700) is illustrated. The system (700) can operate similarly to the system (400) discussed above. Specifically, the system (700) can include the supply spout (704) being a shower head, with a reservoir (706) suspended from the supply spout (704) to receive water (102) from the supply spout (704). The reservoir (706) may supported in one or more other ways during use. For example, the reservoir (706) may be suspended from the supply spout (704), held by a user, and/or set on a shower floor or tub side in different flushing operations and/or at different times during the same flushing operation. The reservoir (706) can include an overflow drain (710) that can drain into a bottom of the shower, which can act as an overflow container (708) as with the overflow container (208) discussed above with reference to FIG. 2. The system (700) can include the pump (120), with the inlet port (124) of the pump (120) being mounted on the reservoir (706) to receive water (102) therefrom. A supply line (730) can extend from the pump (120) to supply water (102) from the pump (120) to an applicator tip (140) mounted on an end of the supply line (730) distal from the pump (120).

II. SUPPLY SPOUT ADAPTER FLUID DISTRIBUTION EXAMPLES

Figure 8:
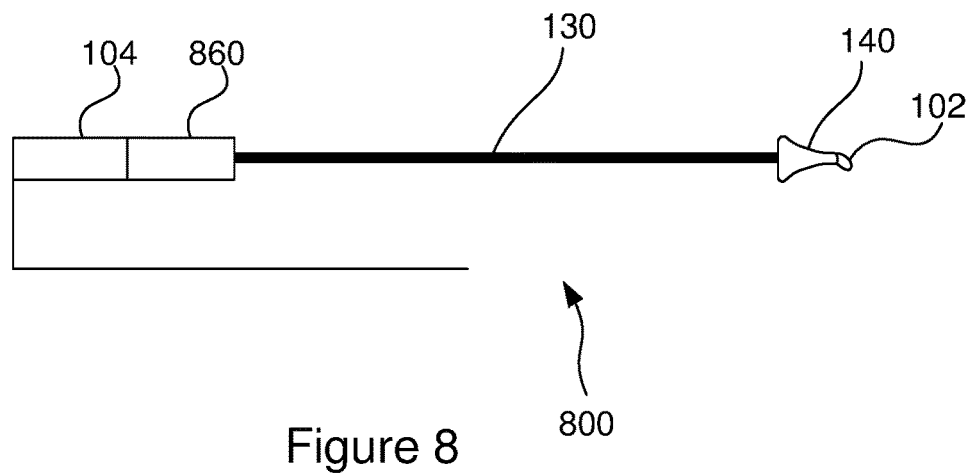
FIG. 8 is a side view of supply spout adapter fluid distribution system.

Referring to FIGS. 8-36, different examples of components for fluid distribution systems with supply spout adapters will be illustrated. The basic components of such a supply spout adapter fluid distribution system (800) for supplying water (102) are illustrated in FIG. 8. The fluid distribution system (800) can include a supply spout (104), though the system (800) may be considered to be just the components beyond the supply spout (104) itself in some examples. The supply spout (104) can be a standard supply spout such as an in-sink bathroom water faucet or a shower head. The system (800) can also include an adapter (860), which can be conformed to seal to any of various different shapes of supply spouts (104). Specifically, the adapter (860) may include at least one sealing surface that is configured to conform to various different shapes of different sealing surfaces of different supply spouts (104). The system (800) can also include a supply line (130), which can be sealed to the adapter (860) at one end and to an applicator tip (140) at another end. Thus, the distribution system (800) can convey pressurized water from the supply spout (104), through the adapter (860), through the supply line (130), and through the applicator tip (140). This can be done while pressurizing the water (102) that leaves the applicator tip (140) by retaining pressure of the water (102) that is supplied to the supply spout (104), such as water pressure from a municipal water system and/or a household water system.

With reference to FIGS. 9-35, embodiments of distribution systems will be discussed with different adapters. In the Figures, at least a portion of the supply lines and applicator tips are not illustrated for the sake of simplicity. However, as will be discussed, the adapters are adapted to be connected to supply lines, which are connected to applicator tips, as illustrated in FIG. 8.

Figure 9:
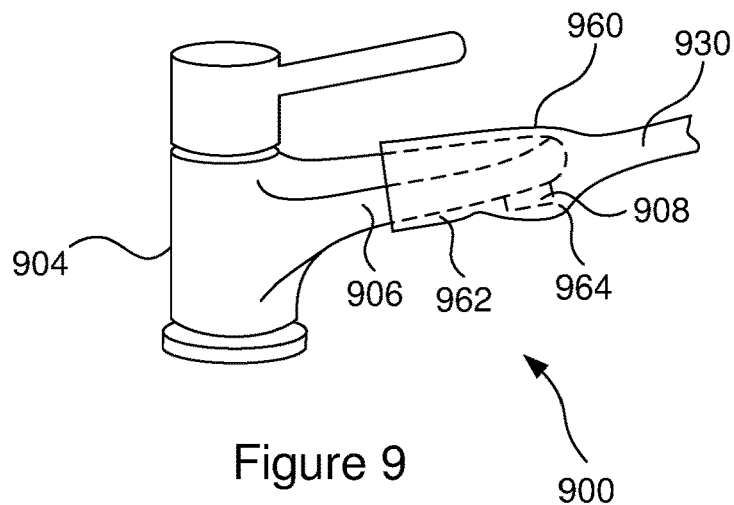
FIG. 9 is a side view of a supply spout adapter fluid distribution system, with some hidden lines shown as dashed lines.

Referring now to FIG. 9, a supply spout adapter fluid distribution system (900) will be discussed. The system (900) can include a supply spout (904), which can be in the form of a standard in-sink bathroom faucet. The supply spout (904) can include a neck (906) that leads to a nozzle (908) (with the nozzle (908) and a portion of the neck (906) being hidden and shown in dashed lines). The system (900) can further include an adapter (960). In this embodiment, the adapter (960) can include a sleeve having elastic properties, such as an elastomeric sleeve that can squeeze around and conform to the neck (906) of the supply spout (904). Thus, an inner surface of a sealing portion (962) of the adapter (960) can be a sealing surface that can form a seal with a sealing surface on the outer surface of the neck (906) of the supply spout (904). As with other fluid seals discussed herein, the seal can be designed to be water tight, though it may allow for some inadvertent leakage. The adapter (960) can include a non-sealing portion (964), which can be positioned around the nozzle (908) of the supply spout (904). Thus, the adapter (960) can be in the form of a conformable sleeve, which can include an elastic sealing portion (962) of the sleeve and a non-sealing portion (964) of the sleeve, with the sealing portion (962) fitting tighter than the non-sealing portion (964). The sealing portion (962) and the non-sealing portion (962) can be integrally formed with each other, or they can be separate parts that are connected and sealed to each other. The non-sealing portion (964) can fit loosely enough around the nozzle (908) to allow water to flow from the nozzle (908) and into the non-sealing portion (964) of the adapter (960). The adapter can be fluidly sealed to an end of a supply line (930), and the water (102) can flow from the non-sealing portion (964) of the adapter (960) to the supply line (930). The remainder of the supply line (930) can lead to an applicator tip (not shown).

Assembly of the system (900) and preparation for use can include sliding the sealing portion (962) of the adapter (960) over the nozzle (908) and onto the neck (906) of the supply spout (904), so that the non-sealing portion (964) of the adapter (960) fits over the nozzle (908). The supply spout (904) can then be turned on to supply water (102) through the non-sealing portion (964) of the adapter (960) and through the supply line (930) to an applicator tip (not shown). After the use is completed, the adapter (960) can be slid off the supply spout (904).

The adapter (960) is illustrated as being an integral part with the supply line (930). However, the adapter (960) and the supply line (930) may be separate parts that are joined by a fluid connector, such as a standard connector for joining two flexible hoses. The adapter (960) may be formed using standard manufacturing techniques such as extrusion and/or molding techniques.

Figure 10:
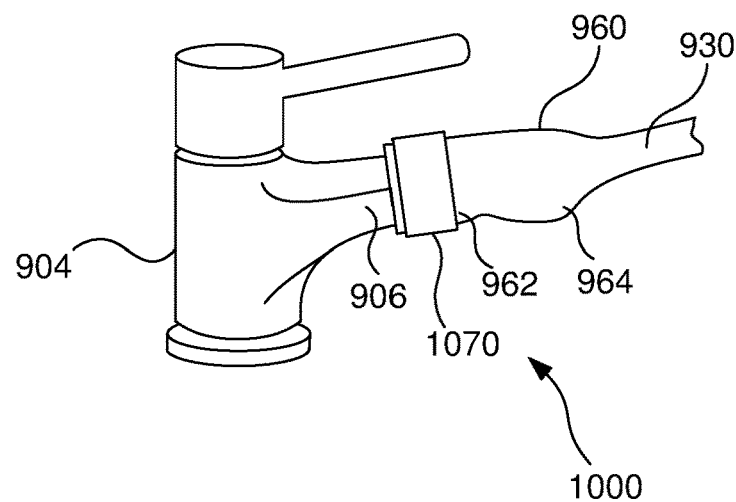
FIG. 10 is side view of another supply spout adapter fluid distribution system.

Referring now to FIG. 10, another example of a supply spout adapter fluid distribution system (1000) is illustrated. The components of the fluid distribution system (1000) of FIG. 10 can be the same as for the fluid distribution system (900) of FIG. 9. However, the adapter (960) can further include a clamp (1070) that can clamp around the sealing portion (962) of the adapter (960). The clamp (1070) may be any of various different type of clamps. For example, the clamp (1070) may be a standard hose clamp, such as a screw/band clamp (worm gear clamp), a spring clamp, or a wire clamp. The clamp (1070) may be an elastomeric band. The system (1000) can be assembled/disassembled and used in the same manner as the system (900) discussed above. However, the clamp (1070) can be clamped onto the sealing portion (962) of the adapter (960) during assembly, and the clamp (1070) can be removed from the sealing portion (962) of the clamp (1070) for disassembly after use of the system (1000).

Figure 11:
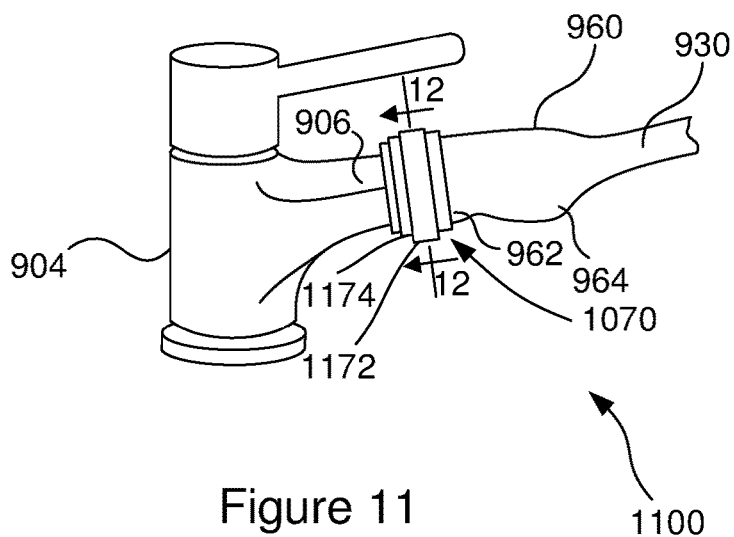
FIG. 11 is side view of yet another supply spout adapter fluid distribution system.
Figure 12:
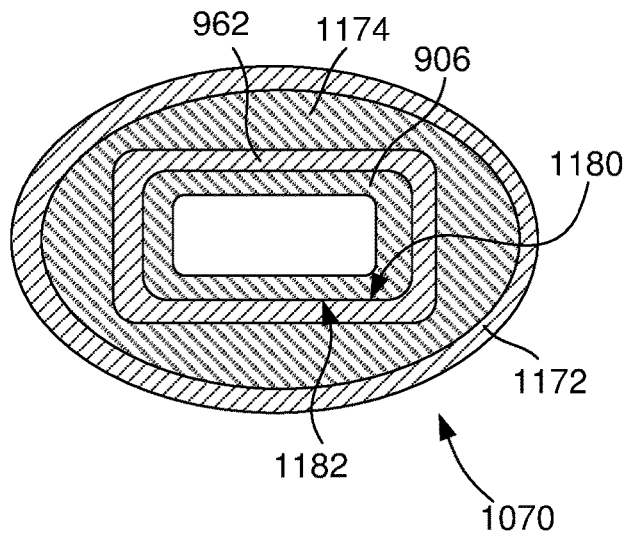
FIG. 12 is a sectional view taken along line 12-12 of FIG. 11.

Referring now to FIGS. 11-12, another example of a system (1100) is illustrated, where the system (1100) is the same as the system (1000) discussed above, except that the clamp (1070) can include a clamp strap (1172) and a compression wrap (1174). For example, the compression wrap (1174) can include a type of memory return contour forming wrap, which can include pressurized fluid sealing features and characteristics. In this example, the clamp strap (1172) can be a type of hose clamp, such as one of the types discussed above. For example, as in the system (900) of FIG. 9, the sleeve of the adapter (960) can be compression set over the supply spout (904), as illustrated in FIG. 9. The compression wrap (1174) can then be applied around the sealing portion (962) of the sleeve of the adapter (960), and the clamp strap (1172) can then be applied around the compression wrap (1174), as illustrated in FIG. 12. The wrap (1174) may be in the form of a non-continuous compressive tape, or in some other form, such as a continuous ring that can be stretched and applied over the sleeve of the adapter (960). The wrap (1174) can be formed of a conforming material such as a foam rubber material. The wrap (1174) may be a different combination of one or more densities and/or materials to apply more or less force to a faucet cross section, such as depending on the faucet general cross-sectional shape. The wrap (1174) may be configured for a general type of cross-sectional shape of supply spout necks (906). Accordingly, the system (1100) may include multiple different wraps (1174) for different general types of cross-sectional shapes of supply spout necks (906). When compressive hoop stresses generated by the clamp mechanism such as clamp strap (1172) are applied down through the wrap (1174), the wrap (1174) can conform to the spout cross-sectional contour, as seen in FIG. 12. This can allow for more uniform compressive force to be applied radially about the neck (906) of the supply spout (904). This can result in a better seal between a sealing surface (1180) of the adapter (960) and a corresponding sealing surface (1182) of the neck (906) of the supply spout (904).

In alternative embodiments, the adapter (960) could be designed with the wrap (1174) configured on the inside of the sealing portion (962) of the adapter (960), on the outside of the sealing portion (962), or combinations thereof. In one example, the wrap (1174) may be applied to the neck (906) of the supply spout (904), and then the sleeve of the adapter (960) may be applied over the wrap (1174), with a clamp ring then being clamped over the sleeve of the sealing portion of the adapter (960). Alternatively, the clamp parts could be configured in other configurations that apply sufficient clamping force to form a seal between a sealing surface of the adapter and a sealing surface of the supply spout.

Figure 13:
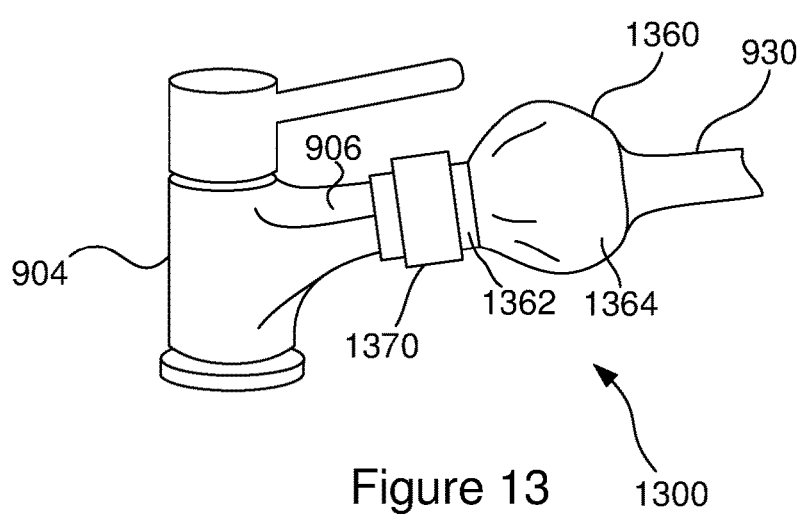
FIG. 13 is a side view of yet another supply spout adapter fluid distribution system.

Referring now to FIG. 13, another example of a supply spout adapter fluid distribution system (1300) will be discussed. The system (1300) of FIG. 13 is similar to the system (1100) of FIGS. 10-12, except that the adapter (1360) includes a sealing portion (1362) the includes a compression ring and a non-sealing portion (1364) that forms a pouch. The sealing portion (1362) can be attached to the non-sealing portion (1364). The compression ring of the sealing portion (1362) can be an elastic compression ring that can be designed to stretch open wide enough to fit over a wide variety of differently-shaped supply spouts, such as differently shaped faucet nozzle assemblies. The pouch of the non-sealing portion (1364) can allow for clearance about the nozzle (908) of the supply spout (904). Additionally, the pouch of the non-sealing portion (1364) can act as a temporary enclosed reservoir, which may absorb pressure spikes and/or provide hydraulic head advantage for increased system pressure. The adapter (1360) can further include a clamp (1370), which can apply additional pressure on the sealing portion (1362) of the adapter (1360).

Figure 14:
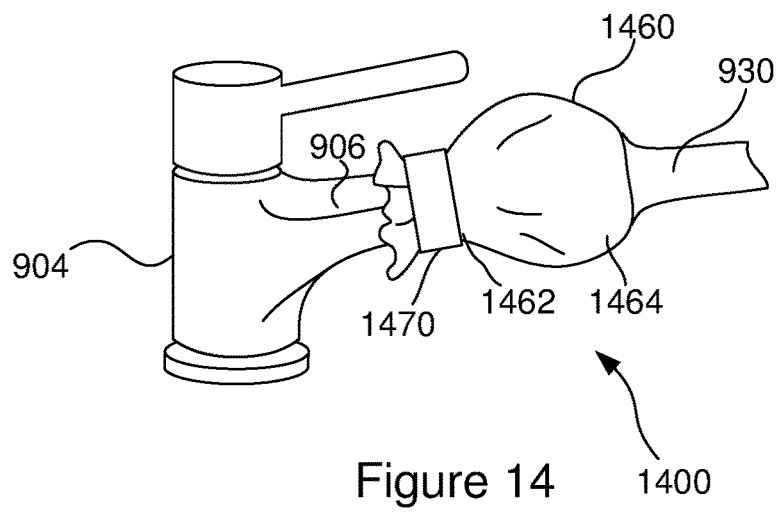
FIG. 14 is a side view of yet another supply spout adapter fluid distribution system.

Referring to FIG. 14, another example of a supply spout adapter fluid distribution system (1400) can be similar to the system (1300) of FIG. 13. However, the adapter (1460) of FIG. 14 can omit the compression ring for the sealing portion (1462), with the pouch of a non-sealing portion (1464) being squeezed in by a clamp (1470) to form the sealing portion (1462).

Referring to FIGS. 15-18, another example of a supply spout adapter fluid distribution system (1500) will be discussed. The system (1500) can include an adapter (1560) that is configured to be useable with differently shaped supply spouts, such as the supply spout (904). The adapter (1560) can seal to the nozzle (908) of the supply spout (904), to transmit pressurized water from the supply spout (904) to a supply line (1530). The adapter (1560) can include an adapter housing (1562), which can be a sleeve that is closed at one end and open at the other end. The adapter housing (1562) can be formed of a rubber-like material, such as an elastomer with rubber-like qualities, which can allow the adapter housing (1562) to conform to differently shaped supply spouts. Alternatively, the adapter housing (1562) may be formed of a more rigid material.

The adapter (1560) can further include a stopple (1564) that is secured within the housing (1562). The stopple (1564) can be formed of a material that can seal to a supply spout nozzle. For example, the stopple (1564) may be formed of a rubber-like material, such as an elastomer with rubber-like qualities. The adapter (1560) can define a hole (1566) that passes through the stopple (1564), through the housing (1562), and to the supply line (1530) to supply water from the supply spout (904) to the supply line (1530). The stopple (1564) can define a sealing surface (1568) around the hole (1566).

Figure 15:
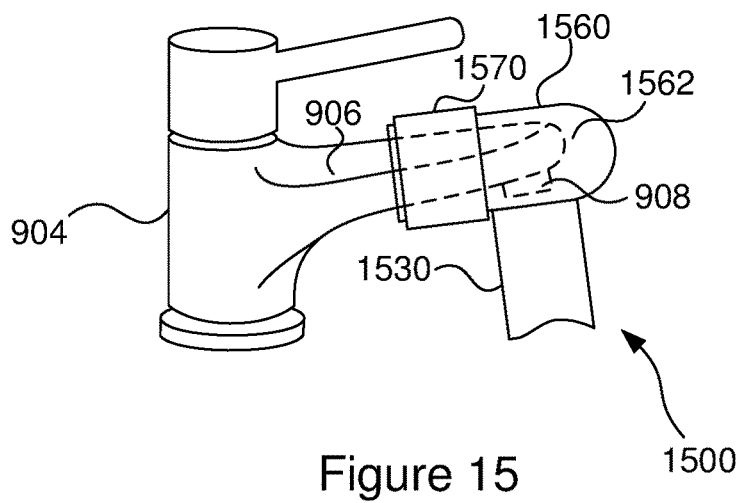
FIG. 15 is a side view of yet another supply spout adapter fluid distribution system, with some hidden lines shown as dashed lines.
Figure 16:
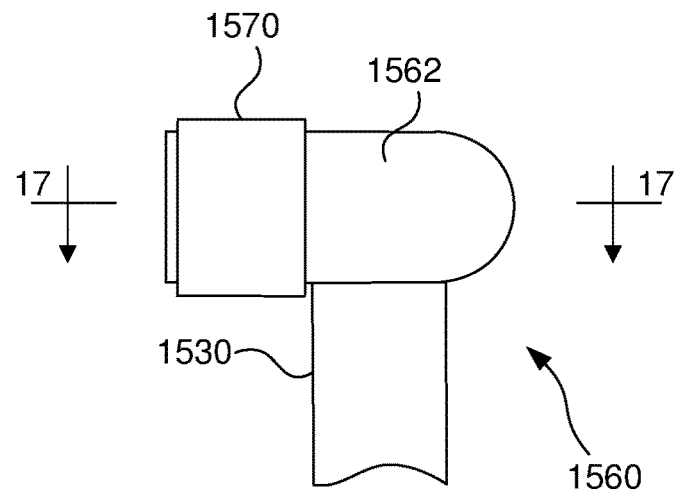
FIG. 16 is a side view of a source adapter of the supply spout adapter fluid distribution system of FIG. 15.
Figure 17:
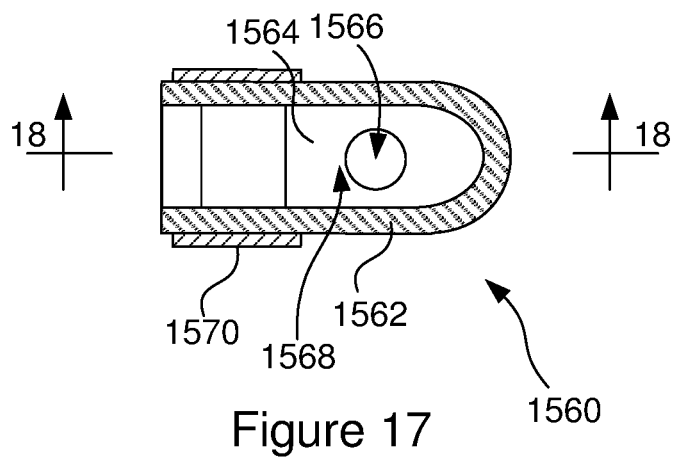
FIG. 17 is a sectional view taken along line 17-17 of FIG. 16.
Figure 18:
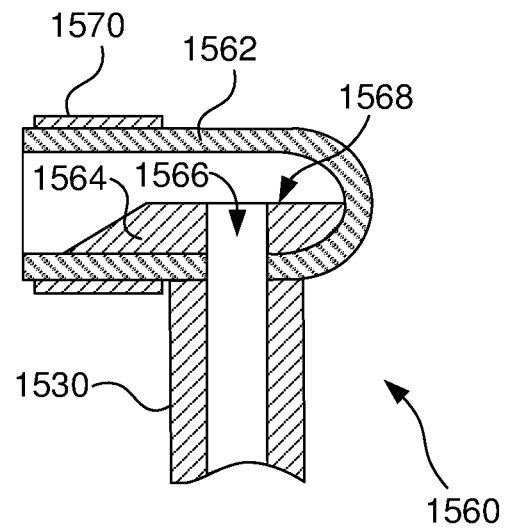
FIG. 18 is a sectional view taken along line 18-18 of FIG. 17.

When in use, the nozzle (908) and a portion of the neck (906) of the supply spout (904) can extend into the housing (1562) (see FIG. 15). In this configuration, a terminus of the nozzle (908) of the supply spout (904) can press against the sealing surface (1568) of the stopple (1564) (with the terminus of the nozzle (908) forming a sealing surface of the supply spout (904)). The adapter (1560) can further include a clamp (1570) that can extend around the housing (1562) where the housing (1562) is extending around the neck (906) of the supply spout (904), to squeeze the housing (1562) onto the neck (906) and hold the adapter (1560) in place relative to the supply spout (904). Instead of or in addition to extending around the housing (1562) at the neck (906) of the supply spout (904), the clamp (1570) may extend below the housing (1562) around the supply line (1530) and may extend above the housing (1562) at an area above the supply line (1530) and the hole (1566). Such a clamp (1570) may squeeze the housing (1562) to press the stopple (1564) against a terminus of the nozzle (908) of the supply spout (904). Thus, in some embodiments, the clamp (1570) may seal the adapter (1560) to the neck (906) and/or the nozzle (908) of the supply spout (904). The housing (1562), stopple (1564), and at least a portion of the supply line (1530) can all be formed as a single member. Alternatively, one or both of the stopple (1564) and supply line (1530) can be formed as separate members that are attached to the housing (1562), with fasteners (e.g., mechanical fasteners and/or adhesives) and/or connectors (e.g., fluid line fittings).

In using the system (1500), the adapter housing (1562) can be slid onto the supply spout (904) until the nozzle (908) of the supply spout (904) aligns with the sealing surface (1568) and the hole (1566) of the adapter (1560). The clamp (1570) can be tightened around the housing (1562) to clamp the housing (1562) onto the neck (906) of the supply spout (904). The supply spout (904) can then be turned on to supply pressurized water from the supply spout (904), through the adapter (1560), through the supply line (1530), and to an applicator tip (not shown) at an end of the supply line (1530) opposite the adapter (1560).

Figure 19:
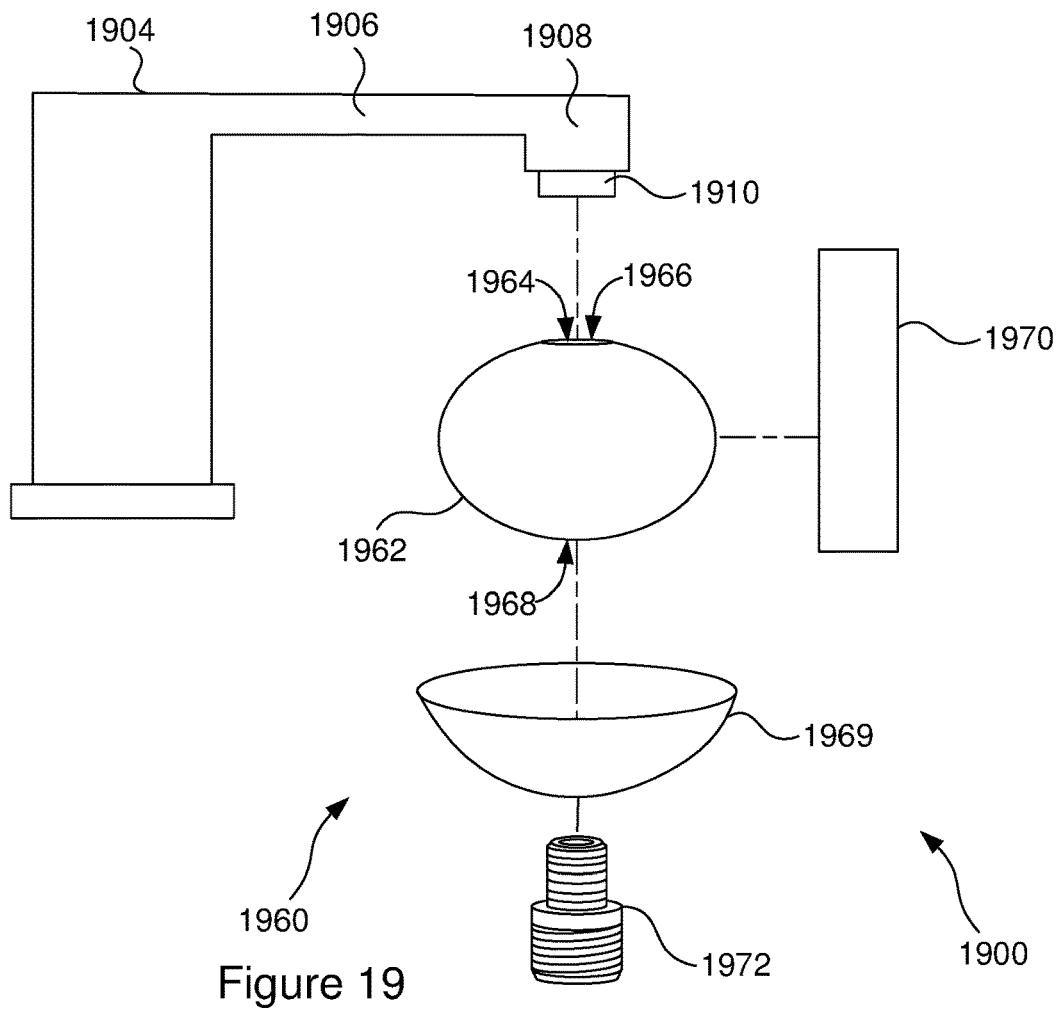
FIG. 19 is an exploded side view of yet another supply spout adapter fluid distribution system.
Figure 20:
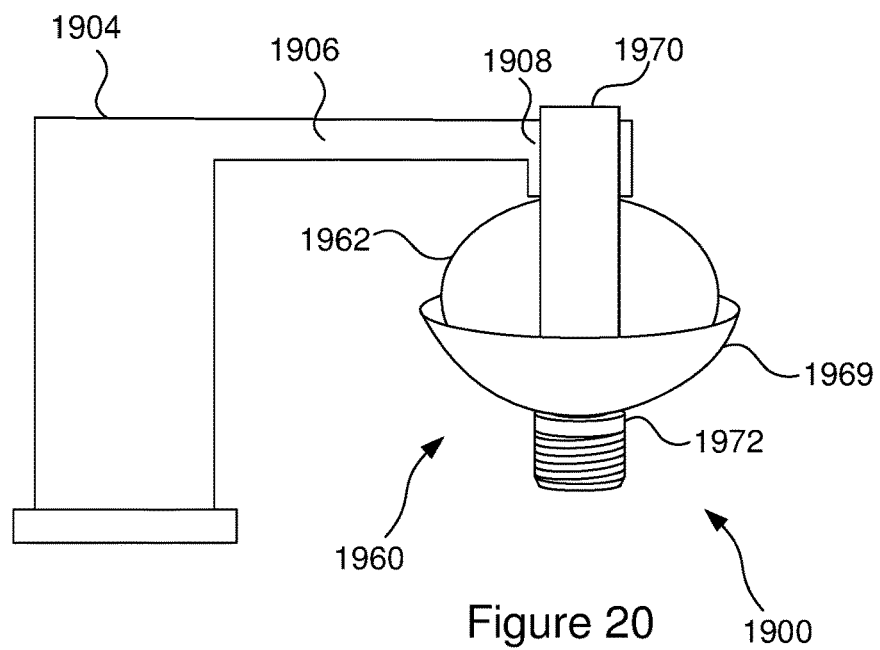
FIG. 20 is an assembled side view of the supply spout adapter fluid distribution system of FIG. 19.

Referring now to FIGS. 19-20, yet another supply spout adapter fluid distribution system (1900) will be discussed. The system (1900) can include a supply spout (1904), which can include a neck (1906) that leads to a head (1908), with a nozzle (1910) extending down from the head (1908). The system (1900) can also include an adapter (1960), which can be secured to a supply line (not shown). The adapter (1960) can include a stopple gasket (1962). For example, the stopple gasket (1962) can be a generally three-dimensionally rounded shape, such as a generally spherical type shape, with the stopple gasket (1962) defining a hole (1964) passing downwardly through the stopple gasket (1962) from an upper spout end (1966) of the hole (1964) to a lower supply line end (1968) of the hole (1964). The spout end (1966) of the hole (1964) can be sized to fit tightly over the nozzle (1910), and indeed to stretch and conform to fit over a variety of different nozzle designs. Thus, the outer cylindrical surface of the nozzle (1910) can form a supply spout sealing surface, which can seal to an inner sealing surface of the stopple gasket (1962) that defines a portion of the hole (1964).

A pressure dish (1969) can be a generally rounded shaped dish that is shaped so that a concave surface of the dish (1969) fits a lower convex surface of the stopple gasket (1962). The pressure dish (1969) can define a central hole therein (not shown) that aligns with the lower supply line end (1968) of the hole (1964) in the stopple gasket (1962). A clamp (1970) can extend around the stopple gasket (1962) and around the head (1908) of the supply spout (1904). Additionally, a connector (1972) can pass through the hole in the dish (1969), through a hole (not shown) in the clamp (1970) and into the stopple gasket (1962). Additionally, the connector (1972) can be secured to the clamp (1970), such as by being threaded into the hole in the clamp (1970). Thus, the dish (1969), which is secured to the clamp (1970) by the connector (1972) can distribute clamping pressure from the clamp (1970) around a larger area of the stopple gasket (1962) to securely hold the stopple gasket (1962) onto the supply spout (1904). The connector (1972) can also be configured to be connected to a supply line (not shown), which can be connected to an applicator tip (not shown) distal from the adapter (1960) and supply spout (1904).

In assembling the system (1900), the stopple gasket (1962) can be pressed onto the nozzle (1910) of the supply spout (1904). The clamp (1970) can be placed around the stopple gasket (1962) and the head (1908) of the supply spout (1904). The dish (1969) can be positioned against the bottom of the clamp (1970) and the stopple gasket (1962) with the concave side of the dish (1969) facing upwardly, and with the hole in the dish aligning with the hole (1964) in the stopple gasket (1962). The connector (1972) can be secured to the clamp and extend into the hole (1964) in the stopple gasket (1962), with the stopple gasket (1962) sealing around the connector (1972). The supply line (not shown) can be secured to the connector (1972), and an applicator tip (not shown) can be secured to the supply line distal from the connector (1972).

In using the system (1900), the supply spout (1904) can be turned on. This can result in pressurized water being supplied from the supply spout (1904), through the adapter (1960), through the supply line, and through the applicator tip. To cease using the system (1900), the supply spout (1904) can be turned off. The system (1900) can then be disassembled by reversing the steps discussed above for assembly of the system (1900).

Figure 21:
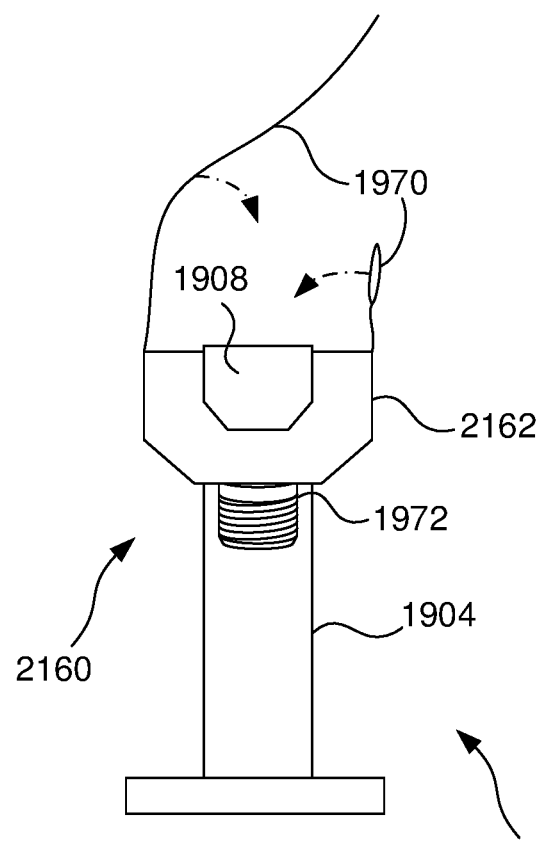
FIG. 21 is a front view of another supply spout adapter fluid distribution system.

Referring now to FIG. 21, another supply spout adapter fluid distribution system (2100) will be discussed, with a front view of the supply spout (1904) instead of a side view. The system (2100) can be the same as the system (1900), except that the stopple gasket (2162) of the adapter (2160) can be a different shape, as compared to the rounded bulbous stopple gasket (1962) of the system (1900). The dish (1969) of the system (1900) may also be omitted. Of course, the stopple gasket may be any of various different shapes, so long as it is configured to be secure to and seal with the supply spout and the supply line (possibly via one or more connectors, such as the connector (1972)). In FIG. 21, the clamp (1970) is illustrated as a strap, such as a strap with a hook-and-loop fastener, although other types of clamps could be used. The dashed arrows in FIG. 21 illustrate movement of the strap of the clamp (1970) toward a clamped position.

III. ADAPTER DISTRIBUTION EXAMPLES WITH FLUID PRESSURE ACTUATED CLAMPS

Several examples of fluid distribution systems with fluid pressure actuated clamps are discussed below. These clamps can be useful in applications outside the specific fluid distribution systems discussed herein. For example, some such clamps may be useful in applying clamping pressure to a sleeve that is joining two pipes together for fluid to flow between the pipes in any of various different applications.

Figure 22:
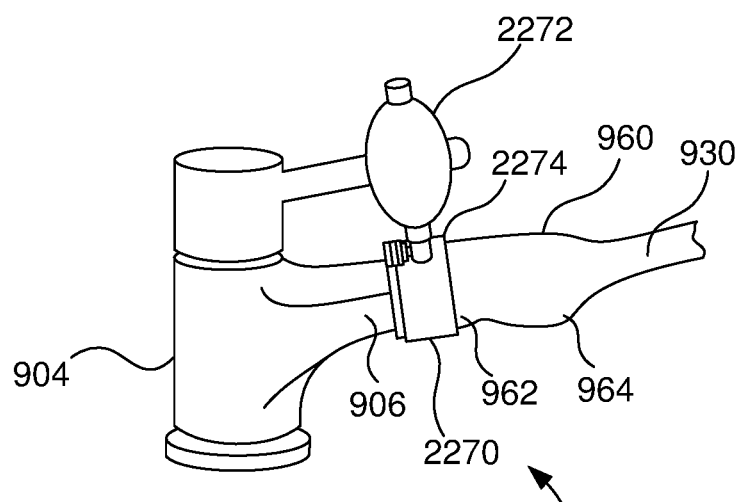
FIG. 22 is a side view of yet another supply spout adapter fluid distribution system.

Referring now to FIG. 22, a supply spout adapter fluid distribution system (2200) is illustrated. The system (2200) can be similar to the adapter fluid distribution system (1000) of FIG. 10, discussed above. As discussed above with regard to the system (1000), the clamp (1070) of the system (1000) could be any of various different types of clamps. In the system (2200), the clamp can be a fluid actuated clamp (2270). The clamp (2270) can include a pressurized fluid supply source (2272), such as a squeeze bulb, which can be similar to squeeze bulbs used for existing hand-held blood pressure cuffs. In some embodiments, the pressurized fluid supply source (2272) could be some other type of source, such as a handheld pump similar to pumps used to pressurize balls. Also, the pressurized fluid supply source (2272) could supply some other type liquid or gaseous fluid other than air. The pressurized fluid supply source (2272) can supply pressurized fluid to a clamping strap (2274), to squeeze the clamping strap more tightly onto the sealing portion (962) of the adapter (960). In some embodiments, the pressurized fluid can be provided to one or more bladders in the strap (2274).

Figure 23:
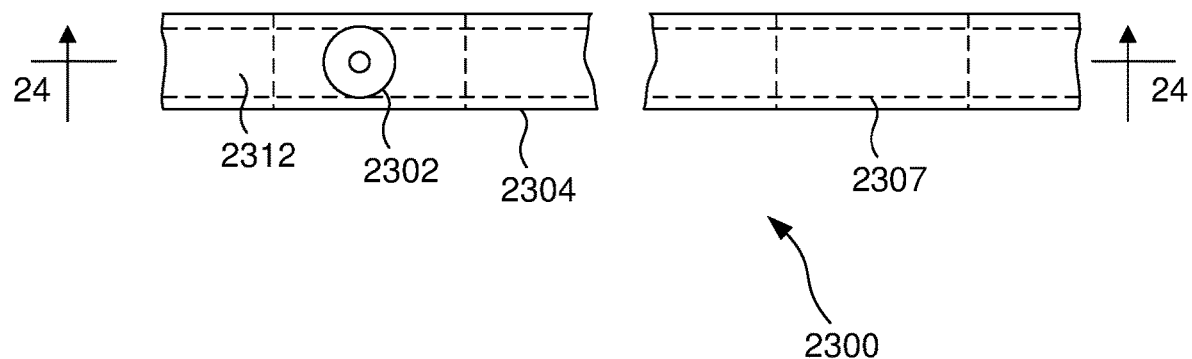
FIG. 23 is a broken away view of a fluid-actuated clamp.
Figure 24:
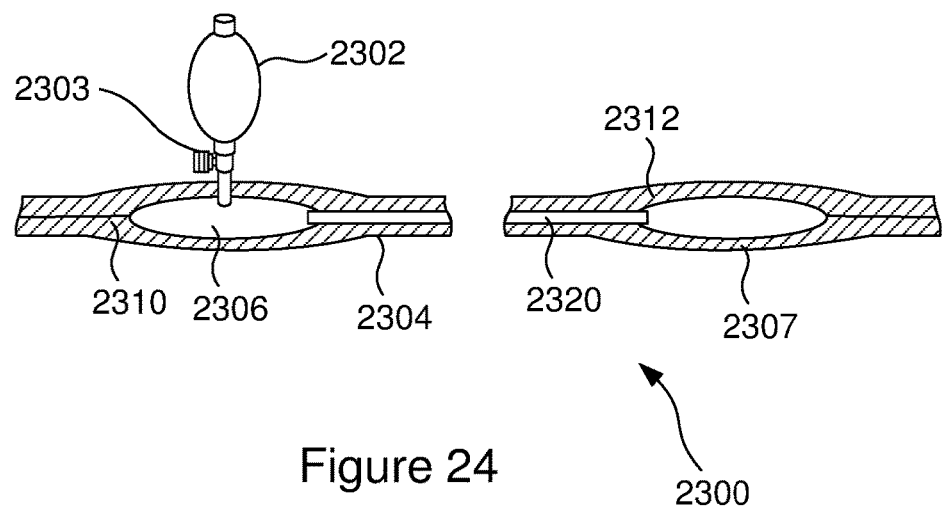
FIG. 24 is a partially sectioned view taken along line 24-24 of FIG. 23.

One example of such a clamp (2300) is illustrated in FIGS. 23-24. In these examples, the clamp (2300) includes a squeeze bulb (2302) that can supply pressurized fluid to a strap (2304). The strap (2304) can include a series of bladders (2306) spaced circumferentially around the strap (2304). The strap (2304) can include an inner layer (2310) of strap material and an outer layer (2312) of strap material, with the bladders (2306) sandwiched between the layers, and with stitching (2307) holding the bladders (2306) in place in the strap (2304). Each of the bladders (2306) can be formed of a stretchable material, such as an elastomeric material. The strap (2304) can also include conduits (2320) that can extend between the bladders (2306), so that fluid can flow between the bladders (2306), which can even out pressure between the bladders (2306). The conduits (2320) can be formed of a material that is flexible enough to curve when the clamp (2300) is curved around a body to be clamped, without cutting off flow within the conduits (2320). However, the conduits (2320) can be formed of material that is sufficiently rigid to withstand fluid pressures from the squeeze bulb (2302).

In use, the clamp (2300) can be placed around an object to be clamped, such as the sealing portion (962) of the adapter (960) of the system (2200). The strap (2304) of the clamp (2300) can be secured by one or more fasteners, such as a buckle or hook-and-loop fasteners. The squeeze bulb (2302) can be repeatedly squeezed to provide pressurized fluid to the bladders (2306), thereby expanding the bladders (2306). The expanding bladders (2306) can stretch the inner layer (2310) of the strap (2304), to squeeze inwardly on the object to be clamped, such as the sealing portion (962) of the adapter (960) of the system (2200). To release the clamp (2300), a release valve for the squeeze bulb (2302) can be opened, such as by turning a handle (2303) of the release valve. The strap can then be removed from the body being clamped.

Referring to FIGS. 25-27, another example of a clamp (2500) will be discussed. The clamp (2500) can include a squeeze bulb (2502) and a strap (2504), as in the clamp (2300). The strap (2504) can include a single bladder (2506) extends around the inside of an outer layer (2507). The outer layer (2507) can be formed so that it is more rigid than the bladder (2506), so that pressure in the bladder (2506) causes the bladder (2506) to squeeze inwardly from the outer layer (2507). The bladder (2506) can be stitched to the outer layer (2507) with stitching (2508). The stitching (2508) can be located in an area of the bladder (2506) that is to the side of an open area of the bladder (2506) that includes a fluid reservoir of the bladder (2506), so that the stitching process will not puncture the bladder (2506), which could cause leaking. The clamp (2500) can operate similarly to the clamp (2300) discussed above.

Referring now to FIG. 28, another example of a supply spout adapter (2860) will be discussed. The adapter (2860) can be similar to the adapter (1560) discussed above, but can additionally include a diaphragm (2880) defining a bladder (2882) inside the housing (1562) above the stopple (1564). A squeeze bulb (2884) can be fluidly connected to the bladder (2882) to supply pressurized fluid to the bladder (2882) while the adapter (1560) is positioned on a supply spout. The squeeze bulb (2884) can be squeezed to pressurize and expand the bladder (2882), so that the bladder applies pressure between the housing (1562) and the supply spout. This pressure can press the nozzle of the supply spout downwardly against the stopple (1564) to more securely seal the adapter (2860) to the supply spout.

Figure 29:
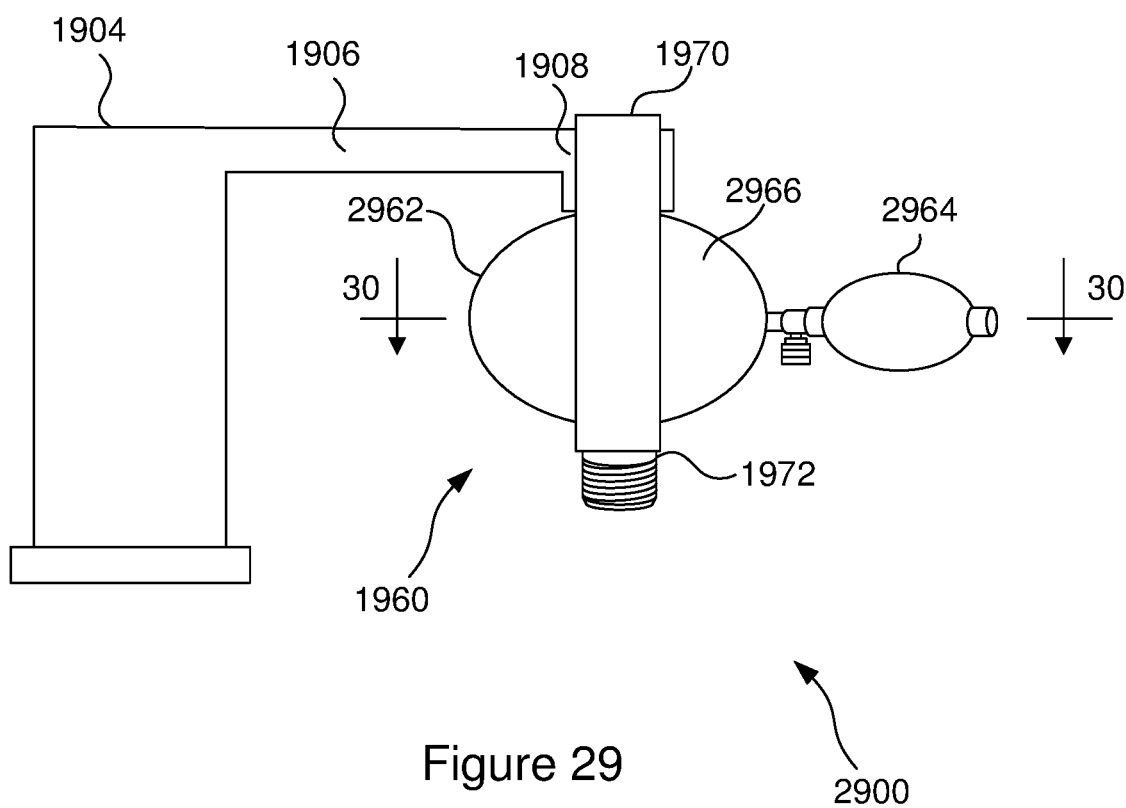
FIG. 29 is a side view of yet another supply spout adapter fluid distribution system.
Figure 30:
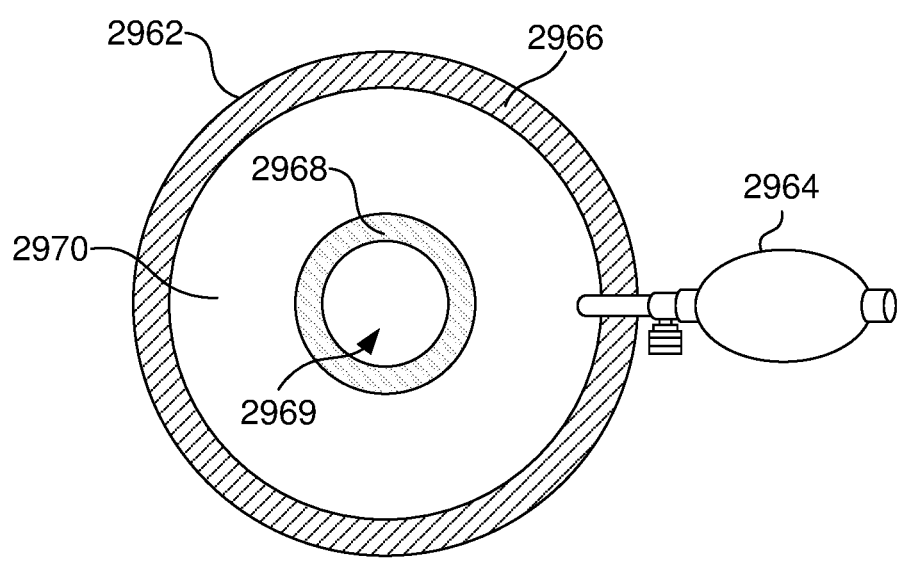
FIG. 30 is a partially sectioned view taken along line 30-30 of FIG. 29.

Referring to FIGS. 29-30, another example of a supply spout adapter fluid distribution system (2900) is discussed. The system (2900) can be the same as the system (1900) discussed above, except that the dish (1969) can be omitted and/or the adapter (1960) can be modified to incorporate a fluid pressure actuated clamp. Specifically, a bulbous stopple gasket (2962) (in place of the stopple gasket (1962) in the system (1900)) can receive pressurized fluid from a squeeze bulb (2964). The stopple gasket (2962) can include an outer shell (2966) with a hole in the top and bottom of the shell (2966). A cylindrical member (2968) can extend from the top to the bottom of the shell (2966), extending circumferentially about the top and bottom holes of the shell (2966), thereby defining a bladder (2970) between the shell (2966) and the cylindrical member (2968). Additionally, the cylindrical member (2968) can define a conduit (2969) therein that can transmit water (102) from the supply spout (1904) to the connector (1972). The shell (2966) may be formed so that it is more rigid than the cylindrical member (2968). Accordingly, when pressurized fluid is provided from the squeeze bulb (2964) into the bladder (2970), the cylindrical member (2968) can squeeze inwardly, more securely sealing the stopple gasket (2962) to the nozzle (1910) of the supply spout (1904) and to the connector (1972). Pressure may be released with the squeeze bulb (2964), as discussed above, after use of the system (2900) and prior to disassembly of the system (2900).

Figure 31:
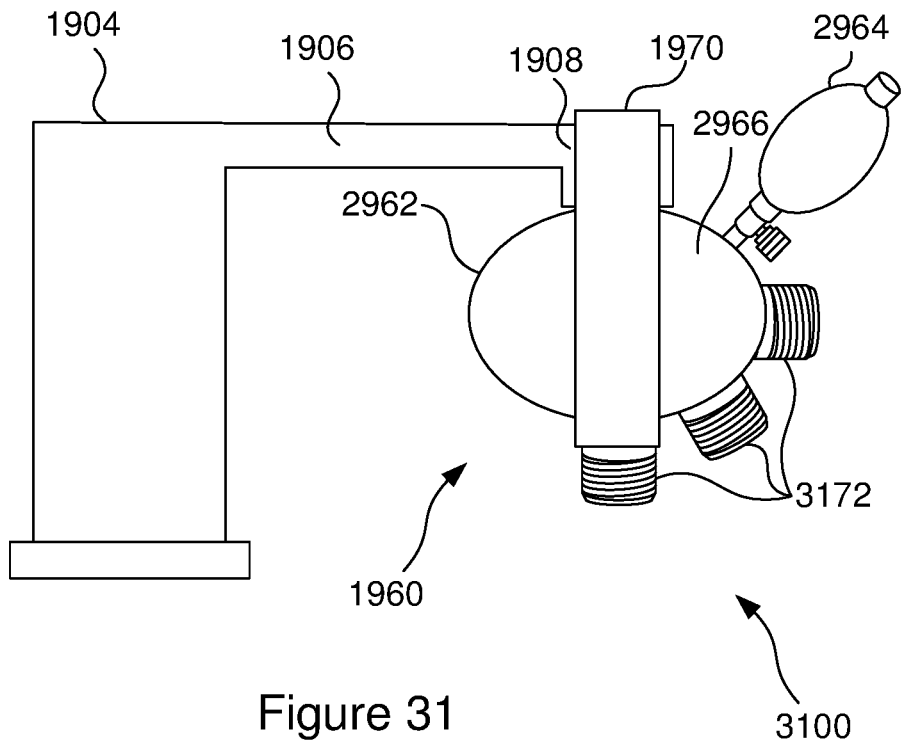
FIG. 31 is a side view of yet another supply spout adapter fluid distribution system.

Referring to FIG. 31, another supply spout adapter system (3100) will be discussed. The system (3100) can be the same as the system (2900), except that that system can include multiple connectors (3172) extending from the adapter (1960), which can each be fluidly connected to the top hole of the bulbous stopple gasket (2962) via internal channels (not shown, but similar to the cylindrical member (2968) of the system (2900)) in the stopple gasket (2962)). These multiple connectors (3172) can allow for connection to multiple different supply lines and/or use water directly from the connectors (3172) at the same time. Connectors (3172) that are not being used may be plugged or capped.

Figure 32:
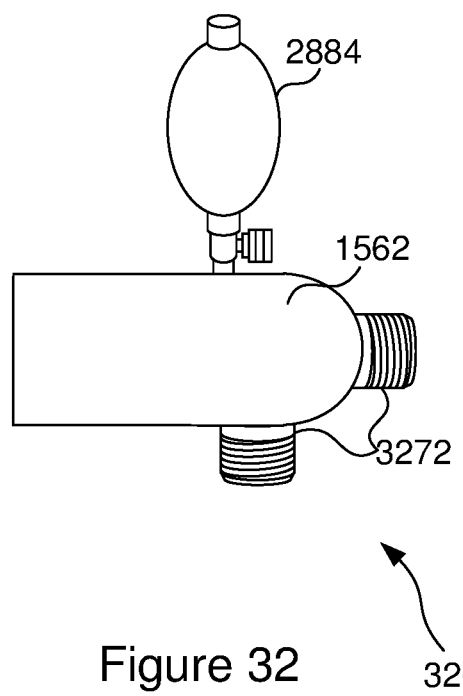
FIG. 32 is a side view of a supply spout adapter.

Referring to FIG. 32, another example of an adapter (3260) will be discussed. The adapter (3260) can be similar to the adapter (2860) discussed above with reference to FIG. 28. However, the adapter (3260) of FIG. 32 can include multiple connectors (3272) extending from the housing (1562) of the adapter (3260). These connectors (3272) can function similarly to the connectors (3172) in the system (3100) of FIG. 31.

Figure 33:
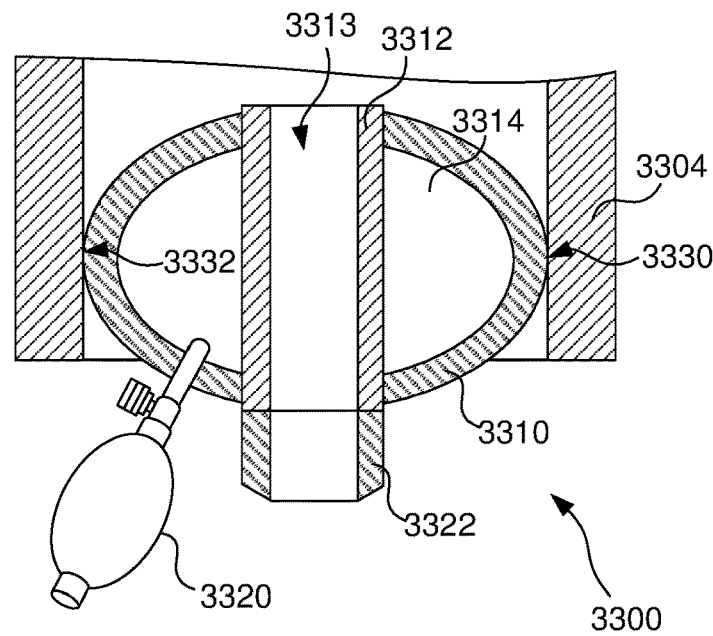
FIG. 33 is a sectional view of yet another supply spout adapter fluid distribution system.

Referring now to FIG. 33, another example of a fluid distribution system adapter (3300) will be discussed. The adapter (3300) can fit into a nozzle (3304) of a supply spout. The adapter (3300) can include a bulbous shell (3310) that can define top and bottom holes therein. A hollow cylindrical member (3312) can extend from the top to the bottom holes of the shell (3310). Thus, the adapter (3300) can define an inner conduit (3313) through which water (102) can pass through the adapter (3300), and a bladder (3314) extending around the conduit (3313). The outer shell (3310) may be more easily stretched than the inner cylindrical member (3312). The adapter (3300) can also include a squeeze bulb (3320) that can supply pressurized fluid into the bladder (3314), as with the embodiments discussed above. The adapter (3300) can also include a connector (3322), which can be secured to the cylindrical member (3312) and can be connected to a supply line.

In use, the adapter (3300) can be positioned at least partially within the nozzle (3304), and the squeeze bulb (3320) can be squeezed to pressurize the bladder (3314) and force an adapter sealing surface (3330) of the outer shell (3310) against a surrounding supply spout sealing surface (3332) of the surrounding nozzle (3304). Accordingly, the adapter (3300) includes a pressure actuated clamp that acts by pushing out instead of squeezing in. When the supply spout is turned on, water can be supplied through the conduit (3313) and the connector (3322) of the adapter (3300). After turning off the supply spout, the adapter (3300) can be removed by releasing pressure from the bladder (3314) via the squeeze bulb (3320) and pulling the adapter (3300) out of the nozzle (3304).

IV. ADDITIONAL ADAPTER FLUID DISTRIBUTION FEATURES

Figure 34:
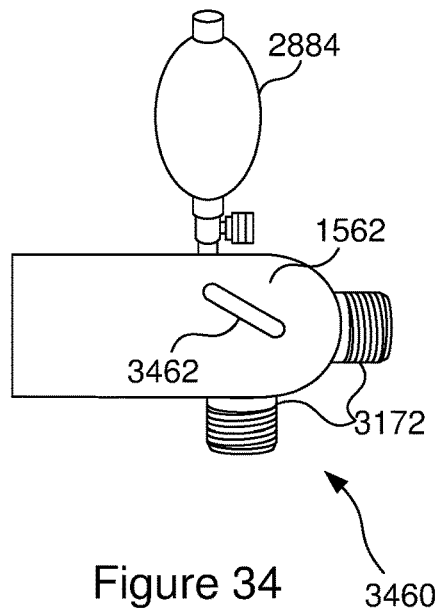
FIG. 34 is a side view of a supply spout adapter.
Figure 35:
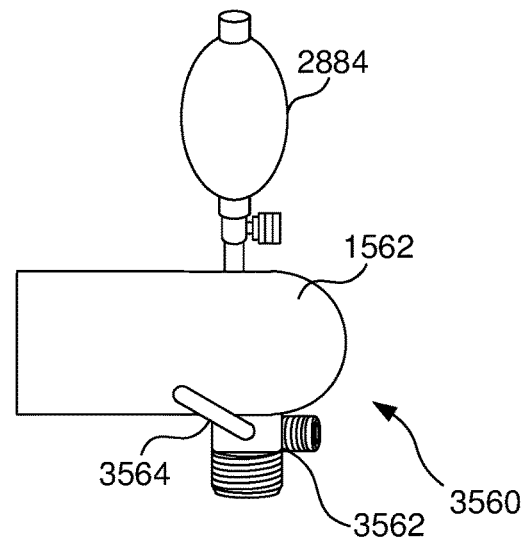
FIG. 35 is a side view of another supply spout adapter.

Referring now to FIG. 34, an adapter (3460) is illustrated, which is similar to the adapter (3260) discussed above, except that the adapter (3460) includes an internal valve operated by a handle (3462) that switches flow between the two connectors (3172). FIG. 35 depicts an adapter (3560) that is similar to the adapter (2860), but with a connector (3562) leading to a supply line, with the connector (3562) incorporating an internal valve operated by a handle (3564) to switch between two outlets of the connector (3562).

Figure 36:
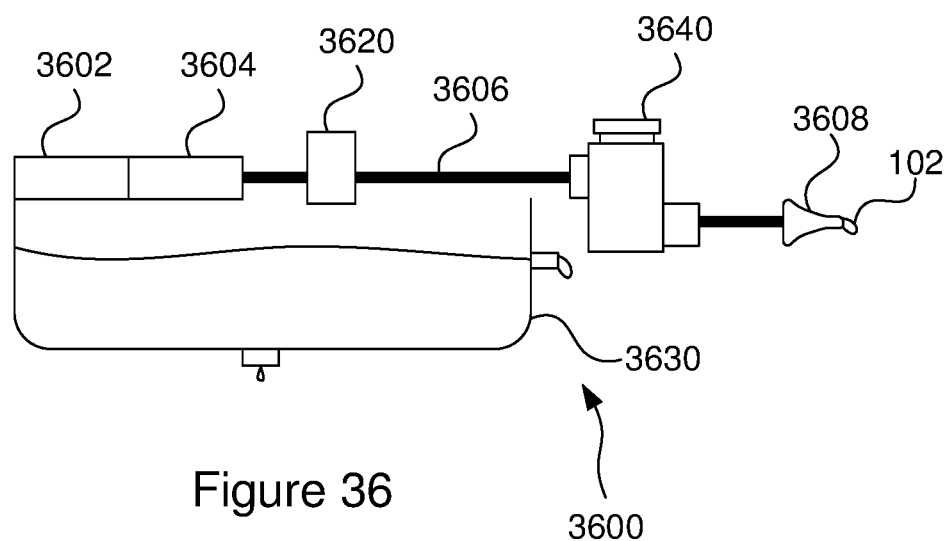
FIG. 36 is a partially sectioned side view of supply spout adapter fluid distribution system.

FIG. 36 illustrates a supply spout adapter fluid distribution system (3600) that includes a supply spout (3602), and an adapter (3604) transmitting pressurized fluid from the supply spout to a supply line (3606). The supply line (3606) can transmit the pressurized fluid to an applicator tip (3608). The system (3600) can further include a pressure relief device (3620) between the adapter (3604) and the applicator tip (3608). For example, the pressure relief device (3620) may be a pressure relief valve, which can empty fluid from the supply line (3606) into a reservoir (3630) if the fluid pressure at the pressure relief device (3620) exceeds a predetermined level. In addition to or instead of the pressure relief device (3620), the system (3600) may include one or more pressure relief devices built into other parts of the system (3600), such as a pressure relief device built into a supply spout adapter.

The system (3600) may also include an inline infuser (3640). A user may load the infuser (3640) with matter to be infused into the water passing through the infuser (3640). For example, the infused matter may be an enema or douche solvent, such as dissolvable tablets, salts, or other forms of diffusible matter. The infusing matter can slowly release into the water flow for application through the applicator tip (3608). The infuser (3640) and/or the pressure relief device (3620) may be incorporated into any of the different embodiments discussed above, such as downstream of a pump in embodiments that include a pump. In addition to or instead of the infuser (3640), the system (3600) may include one or more infusers built into other parts of the system (3600), such as an infuser built into a supply spout adapter. The infusers and/or pressure relief devices may be used with any of the systems described herein, including supply spout adapter and/or reservoir-pump systems. Also, any such systems may include devices that detect flow rate, reservoir level (fluid level in the reservoir), and/or pressure. Output from such detection devices can be used to control pumps and/or flow restricting valves in the system. For example, if the pressure and/or flow rate is too high, and/or the reservoir level is too low, the pump may be slowed down or stopped. Similarly, if the pressure and/or flow rate is too low, and/or reservoir level is too high, the pump may be switched on or speeded up. Likewise, the pump may be started once the reservoir level is sufficiently high. This can allow the system to auto-start, auto-stop, and/or auto-regulate. For example, this may allow a user to use one hand for filling, and another hand to apply the applicator without having to switch the system on and/or off by hand during use.

V. SOURCE-FED APPLICATOR HUB

Figure 37:
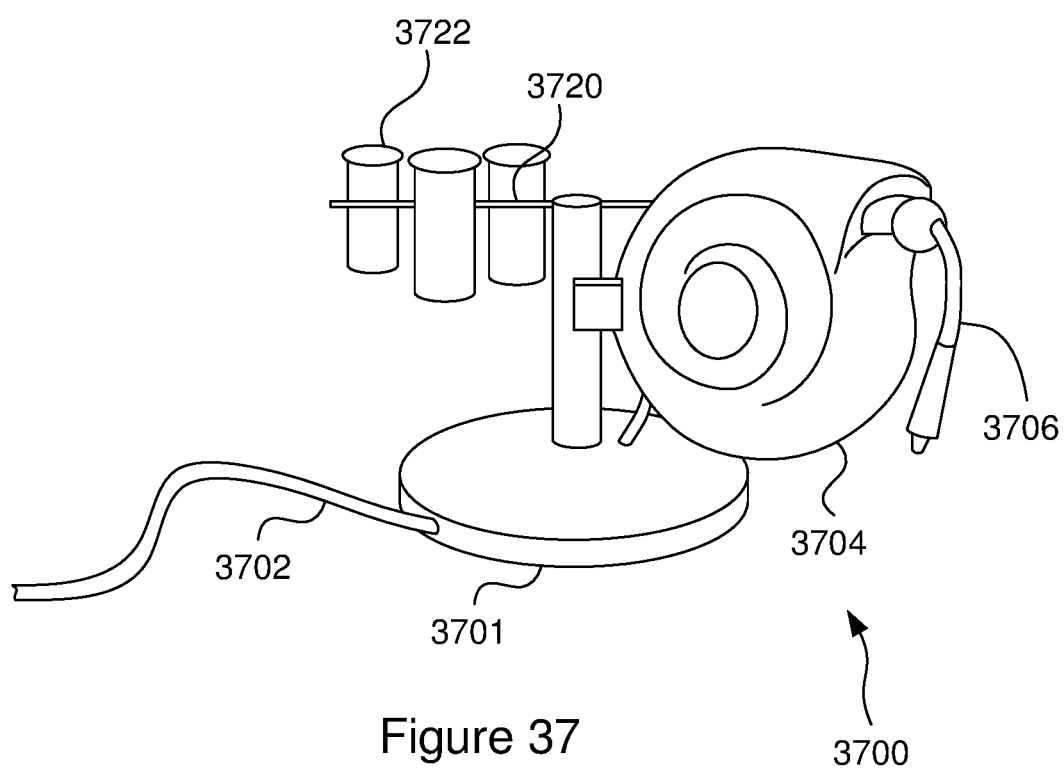
FIG. 37 is a perspective view of a source-fed applicator hub.

Referring now to FIG. 37, a source-fed applicator hub (3700) will be discussed. The hub (3700) can include a base (3701) to which various components can be attached. A feed hose or line (3702) from a pressurizing source (e.g., a spout and adapter, and/or a pump), such as those discussed above can feed into the hub. The feed line (3702) can lead to a retractable line or hose assembly (3704), which can include a retractable distribution line or hose (3706) that is fluidly connected to the feed line (3702). Thus, the feed line (3702) and the distribution hose (3706) can form a supply line as in the embodiments discussed above. At an end of the distribution hose (3706) distal from the feed line (3702), the distribution hose (3706) can include an applicator quick connect/disconnect connector. The hub (3700) may include a plurality of different applicator tips (not shown) that each includes a quick connect/disconnect connector that is configured to be connected and disconnected from the connector on the distribution hose (3706). Thus, different types of applicator tips may be easily connected to and disconnected from the distribution hose (3706).

The hub (3700) can further include an applicator tip support structure (3720), which can be secured to the base (3701) and can support a plurality of applicator tip holders (3722), which can each hold an applicator tip. For example, the holders (3722) can be cup-shaped members, which are supported by the support structure (3720).

The hub (3700) can also include other features, such as hub charge station features available to provide power to powered applicators (for battery charge or directly), e.g. power water pick, enema-douche, or water infused (sonic) vibrating toothbrushes. In other embodiments power could be supplied along the distribution hose (3706) to an applicator connection point, with electrically powered applicators being connected to electrical power upon being connected to the distribution hose.

VI. ASPECTS OF THE EMBODIMENTS

Some aspects of different embodiments are discussed below. Different features of these aspects can be used in different combinations with each other.

A. Technique for Using a Water Fluid Distribution System

A technique for using a water fluid distribution system can include receiving water from a supply spout through an inlet, with the supply spout being one of a water faucet spout or a shower head. The water can be passed through a supply line connected to a personal hygienic flushing applicator tip. The water can also be passed from the supply line and through the applicator tip, with the water that is passed through the applicator tip exiting the water fluid distribution system at the same time as the receiving of the water from the supply spout through the inlet (i.e., some portion of the water can be received from the supply spout through the inlet at the same time as another portion of the water is exiting the water fluid distribution system through the applicator tip). The water can be pressurized using a water pressurizing device, with the passing of the water from the supply spout through the applicator tip including passing the pressurized water through the applicator tip, and with the water pressurizing device including one or more of a powered fluid pump and a source adapter that is fluidly sealed to the supply spout, with the source adapter being conformable to match multiple different shapes of corresponding supply spouts. This technique can be used with combinations of the features discussed below.

The source adapter can have a conformable adapter sealing surface that is conformable to multiple different shapes of supply spout sealing surfaces.

The applicator tip can be a personal hygienic flushing applicator tip and the technique can include utilizing the applicator tip in a personal hygienic flushing operation. For example, the applicator tip may be an enema applicator tip and the technique can include utilizing the applicator tip in an enema operation.

In a situation where the water pressurizing device includes the source adapter (though it may also include a powered pump), the pressurizing of the water can include conveying pressurized water to the supply line from the supply spout while maintaining water pressure that is present in the supply spout, so that at least some of that pressure is conveyed into the supply line and may be conveyed through the applicator tip.

The source adapter can include a clamp, with the clamp pressing an adapter sealing surface against a corresponding source sealing surface of the supply spout. The clamp may be a fluid pressure actuated clamp such as an air clamp. For example, with an air clamp, the technique may include receiving pressurized air in the air clamp to inflate a bladder of the air clamp, with the bladder pressing the adapter sealing surface against the source sealing surface when the bladder is inflated.

Where there is an adapter sealing surface and a source sealing surface, the source sealing surface may be around one or more of a neck of the water faucet spout or a neck of the shower head.

Where there is an adapter sealing surface and a source sealing surface, the source adapter may include a stopple, the source sealing surface may be on a nozzle of the water faucet spout, and the adapter sealing surface may be a stopple surface of the stopple, with the adapter sealing surface being pressed against the source sealing surface to seal the adapter to the supply spout.

Where the water pressurizing device includes the source adapter, the inlet may include the source adapter.

The water pressurizing device may include the fluid pump, and the pressurizing of the water can include engaging the water via the fluid pump. For example, the fluid pump may receive and pressurize water from a non-pressurized fluid reservoir, with the non-pressurized fluid reservoir continuously receiving water from the supply spout while the water is being supplied through the applicator tip.

The receiving of the water from the supply spout, the passing of the water through the supply line, and the passing of the water through the applicator tip can include continuously passing the water from the supply spout through the supply line and the applicator tip while the applicator tip is being used to apply the water to a human body part.

The applicator tip may be a first applicator tip of a first type for applying water to a first type of body part. The technique can include exchanging the first applicator tip for a second applicator tip of a second type that is different from the first type for applying water to a second type of body part that is different from the first type of body part. The technique may further include passing pressurized water through the second applicator tip to the second type of body part via the supply spout, the supply line, and the second applicator tip while performing the pressurizing of the water.

The technique may further include connecting and fluidly sealing the inlet to the supply spout via the source adapter without using tools.

The supply spout can be a first supply spout, and the water can be water received from the first supply spout. The technique may further include fluidly sealing the inlet to the first supply spout via the source adapter, with the adapter sealing surface sealing to a spout sealing surface of the first supply spout and discontinuing receiving the water from the first supply spout. The technique can also include fluidly sealing the inlet to a second supply spout via the source adapter, with an adapter sealing surface of the adapter sealing to a spout sealing surface of the second supply spout, with the spout sealing surface of the second supply spout being a different shape from the spout sealing surface of the first supply spout, and with the second supply spout being one of a water faucet spout or a shower head. The technique can also include receiving water from the second supply spout through the inlet, passing the water from the second supply spout through the supply line, and passing the water from the second supply spout from the supply line and through the applicator tip. The technique can further include pressurizing the water from the second supply spout, with the passing of the water from the second supply spout through the applicator tip comprising passing the pressurized water through the applicator tip.

B. Technique for Fluidly Sealing a First Conduit to a Second Conduit

In additional aspects of the embodiments, a technique can include positioning a first conduit adjacent to a second conduit. The technique can further include fluidly sealing the first conduit to the second conduit. The fluidly sealing can include positioning a fluid clamp in a sealing position. The fluidly sealing can further include, with the fluid clamp in the sealing position, forcing pressurized fluid, such as air, from a pressurized fluid source into a bladder of the fluid clamp. The pressurized fluid can inflate the bladder, with the bladder pressing a pair of sealing surfaces against each other when the bladder is inflated.

The first conduit can be one of an in-sink water faucet spout or a shower head. The second conduit can be a supply line fluidly connected to an applicator tip distal from the first conduit. The technique can include spraying water via the applicator tip, with the sprayed water being received through the supply line from the first conduit. The pair of sealing surfaces can include an adapter sealing surface of a source adapter and a source sealing surface of either the water faucet spout or the shower head, and the adapter sealing surface can be pressed into contact with the source sealing surface by the clamp.

C. A Water Fluid Distribution System

Aspects of embodiments can include a water fluid distribution system. The system can include a water inlet configured to receive water from a supply spout that is one of an in-sink water faucet spout or a shower head. A supply line can be connected to the inlet, and an applicator tip can be connected to the supply line distal from the inlet. The applicator tip can be configured to spray water received through the supply line at the same time as the receiving of the water from the supply spout through the inlet. The system can further include a water pressurizing device that is operable to pressurize water received from the supply spout via the water inlet and supplied through the supply line to the applicator tip. The water pressurizing device can include one or more of a powered fluid pump and a source adapter, with the source adapter having a conformable adapter sealing surface that is conformable to multiple different shapes of corresponding supply spout sealing surfaces.

The applicator tip can be a personal hygienic flushing applicator tip. For example, the applicator tip may be an enema applicator tip. The water pressurizing device can include the source adapter, with the water pressurizing device being configured to convey pressurized water to the supply line from the supply spout. The source adapter can include a clamp that is configured to press the adapter sealing surface against the source sealing surface of the supply spout. The clamp can be an air clamp, with the air clamp being configured to receive pressurized air to inflate a bladder, and with the bladder being configured to press the adapter sealing surface against the source sealing surface when the bladder is inflated. The source sealing surface can be around a neck of the water faucet spout or a neck of the shower head. The source adapter may include a stopple that includes the adapter sealing surface that is adapted to seal with the source sealing surface on a nozzle of the supply spout. Also, the water inlet may include the source adapter.

The water pressurizing device can include the fluid pump. The system may further include a water fluid distribution hub. The hub can include a retractable hose assembly that is configured to retract a hose that forms at least a portion of the supply line, and an applicator tip holder, with the applicator tip holder being configured to hold a plurality of different types of applicator tips that are each configured to releasably and interchangeably connect to the supply line.

The water pressurizing device can include the source adapter. The source adapter may include a plurality of outlets, with one of the outlets being fluidly connected to the supply line.

D. Fluid Pressure Clamp System

Aspects of embodiments can include a fluid pressure clamp system, which can include a fluid clamp. The fluid clamp can include a bladder and a pressurized fluid source connected to the bladder. The clamp can be configured to fluidly seal a first conduit to a second conduit, with the fluid clamp being configured to receive pressurized fluid from the pressurized fluid source to inflate the bladder of the fluid clamp, and with the bladder being configured to press a pair of sealing surfaces against each other when inflated to fluidly seal the first conduit to the second conduit.

The first conduit can be one of an in-sink water faucet spout or a shower head. The assembly can include the second conduit and an applicator tip. The second conduit can be a supply line fluidly connected to the applicator tip distal from the first conduit, with the applicator tip being configured to spray water received through the supply line from the first conduit.

The pair of sealing surfaces can include an adapter sealing surface of a source adapter and a source sealing surface of either the water faucet spout or the shower head. The adapter sealing surface can be configured to be pressed into contact with the source sealing surface by the clamp.

VII. CONCLUSION

The embodiments discussed herein can provide substantial benefits, such as providing a portable system that can be connected to provide water from a supply spout at the same time as providing pressurized water through an applicator tip. This can allow for a system that provides continuous pressurized water for hygienic flushing applications from a supply spout with a distribution system that can be portable and that can connect to differently-shaped supply spouts. This may be done without requiring a large reservoir to be transported with the system. The embodiments can also provide a system that is convenient for using a pressurized fluid distribution system as discussed herein, such as by using the hub discussed above. The embodiments herein can also allow for a system that is easily sanitized. For example, components may be formed of bacteria-resistant materials. Also, in many of the embodiments, contact between a bathroom sink basin and water flowing to the applicator tip can be avoided to help with sanitation. For example, avoiding contact with elements in the sink basin could be particularly advantageous in sinks with which the user is not familiar A user may take steps to sanitize portions of sink basins, supply spouts, etc. with which the water flowing to the applicator tip will make contact in an embodiment of a system being used.

The subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently. Similar rearrangements to systems and components discussed herein may also be made, and different features of systems and/or techniques may be combined in different ways.

While the invention has been particularly shown and described with reference to preferred embodiments thereof, it will be understood by those skilled in the art that various changes in form and details may be made therein without departing from the spirit and scope of the invention. For example, a powered fluid pump can be included in a supply line that extending from a supply spout adapter, so that pressure can be supplied from pressure in the supply spout and that pressure can be increased by the powered fluid pump. Also, the features different systems, components, and techniques related to embodiments discussed herein can be used together in different combinations than the combinations shown and discussed herein.

I claim:

1. A water fluid distribution system comprising:
 a water inlet configured to receive water from a supply spout that is one of an in-sink water faucet spout or a shower head;
 a supply line connected to the inlet;
 an applicator tip connected to the supply line distal from the inlet, with the applicator tip being configured to spray water received through the supply line at the same time as the receiving of the water from the supply spout through the inlet;
 a water pressurizing device that is operable to pressurize water received from the supply spout via the water inlet and supplied through the supply line to the applicator tip, with the water pressurizing device comprising one or more of a powered fluid pump and a source adapter, with the source adapter having a conformable adapter sealing surface that is conformable to multiple different shapes of corresponding supply spout sealing surfaces; and
 a water fluid distribution hub, with the hub including a retractable hose assembly that is configured to retract a hose that forms at least a portion of the supply line, and an applicator tip holder, with the applicator tip holder being configured to hold a plurality of different types of applicator tips that are each configured to releasably and interchangeably connect to the supply line.

2. The water fluid distribution system of claim 1, wherein the applicator tip is a personal hygienic flushing applicator tip.

3. The water fluid distribution system of claim 1, wherein the applicator tip is an enema applicator tip.

4. The water fluid distribution system of claim 1, wherein the water pressurizing device comprises the source adapter, with the water pressurizing device being configured to convey pressurized water to the supply line from the supply spout.

5. The water fluid distribution system of claim 4, wherein the source adapter comprises a clamp that is configured to press the adapter sealing surface against a source sealing surface of the supply spout.

6. The water fluid distribution system of claim 5, wherein the clamp is an air clamp, with the air clamp being configured to receive pressurized air to inflate a bladder, and with the bladder being configured to press the adapter sealing surface against the source sealing surface when the bladder is inflated.

7. The water fluid distribution system of claim 5, wherein the source sealing surface is around a neck of the water faucet spout or a neck of the shower head.

8. The water fluid distribution system of claim 4, wherein the water inlet comprises the source adapter.

9. The water fluid distribution system of claim 1, wherein the water pressurizing device comprises the fluid pump.

* * * * *